United States Patent
Zhang et al.

(10) Patent No.: US 11,491,232 B2
(45) Date of Patent: Nov. 8, 2022

(54) LACTULOSIDE COMPOUNDS AND PREPARATION AND USE THEREOF

(71) Applicant: Fruithy Holdings Limited, Hong Kong (CN)

(72) Inventors: Shanchun Zhang, Anhui Province (CN); Jiashi Peng, Anhui Province (CN); Bin Yang, Anhui Province (CN); Yihua Wang, Anhui Province (CN); Min Xu, Anhui Province (CN); Xiao Wang, Anhui Province (CN); Kaisheng Cheng, Anhui Province (CN)

(73) Assignee: Fruithy Holdings Limited, Hong Kong (CN)

( * ) Notice: Subject to any disclaimer, the term of this patent is extended or adjusted under 35 U.S.C. 154(b) by 37 days.

(21) Appl. No.: 16/489,238

(22) PCT Filed: Mar. 29, 2018

(86) PCT No.: PCT/CN2018/081138
§ 371 (c)(1),
(2) Date: Aug. 27, 2019

(87) PCT Pub. No.: WO2018/177381
PCT Pub. Date: Oct. 4, 2018

(65) Prior Publication Data
US 2020/0009258 A1    Jan. 9, 2020

(30) Foreign Application Priority Data
Mar. 30, 2017   (CN) .......................... 201710205999.7

(51) Int. Cl.
*A61K 47/54* (2017.01)
*A61K 31/52* (2006.01)
*A61K 31/505* (2006.01)
*A61K 31/573* (2006.01)
*A61K 31/4035* (2006.01)
(Continued)

(52) U.S. Cl.
CPC ............ *A61K 47/549* (2017.08); *A61K 9/167* (2013.01); *A61K 9/1611* (2013.01); *A61K 9/1652* (2013.01); *A61K 9/2009* (2013.01); *A61K 9/2018* (2013.01); *A61K 9/2054* (2013.01); *A61K 9/284* (2013.01); *A61K 9/2813* (2013.01); *A61K 9/2846* (2013.01); *A61K 9/485* (2013.01); *A61K 9/4825* (2013.01); *A61K 9/4858* (2013.01); *A61K 9/4866* (2013.01); *A61K 31/4035* (2013.01); *A61K 31/4164* (2013.01); *A61K 31/4468* (2013.01); *A61K 31/505* (2013.01); *A61K 31/52* (2013.01); *A61K 31/573* (2013.01); *A61P 1/00* (2018.01)

(58) Field of Classification Search
CPC ...... A61K 47/549; C07H 19/06; C07H 19/16; C07H 17/02; C07H 17/04; C07H 15/18; C07H 15/26; C07H 15/203; A61P 5/44; A61P 35/00; A61P 1/00
USPC .......................................................... 514/26
See application file for complete search history.

(56) References Cited

FOREIGN PATENT DOCUMENTS

| CN | 110650966 B | 1/2020 |
|---|---|---|
| WO | WO-9415947 A1 | 7/1994 |

(Continued)

OTHER PUBLICATIONS

Oshima et a, J. Gastroenterol 2016, 51, 768-778.*
(Continued)

*Primary Examiner* — Ganapathy Krishnan
(74) *Attorney, Agent, or Firm* — Sterne, Kessler, Goldstein & Fox P.L.L.C.

(57) ABSTRACT

The present disclosure relates to the field of pharmaceutical chemistry, and particularly to a compound represented by Formula (I), a preparation method and medical use thereof. In the compound represented by Formula (I), a lactulosyl group is connected to a heteroatom of genin (G) via a glycosidic bond, wherein the genin (G) is a group formed by removing one hydrogen atom from a heteroatom of an active pharmaceutical molecule, and "~" indicates that the lactulosyl group is connected to the heteroatom of the genin (G) via an α-glycosidic bond or a β-glycosidic bond. Pharmacokinetic experiments prove that the lactuloside compound according to the present disclosure can pass through the gastrointestinal tract of a mammal without being absorbed significantly by the gastrointestinal tract and hydrolyzed significantly by endogenous enzymes of a mammal host. Therefore, the lactuloside compound can arrive at the colon site of the mammal, and release an active drug in the colon under the action of colon flora. The lactuloside compound has a function of colon-localized drug release, and can be used for preventing or treating an intestinal disease.

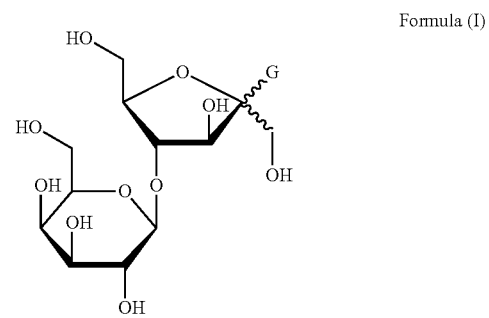

Formula (I)

5 Claims, 4 Drawing Sheets

(51) Int. Cl.
    *A61K 31/4164*      (2006.01)
    *A61P 1/00*      (2006.01)
    *A61K 9/16*      (2006.01)
    *A61K 9/20*      (2006.01)
    *A61K 9/28*      (2006.01)
    *A61K 9/48*      (2006.01)
    *A61K 31/4468*      (2006.01)

(56) References Cited

FOREIGN PATENT DOCUMENTS

| | | |
|---|---|---|
| WO | WO-2010049432 A1 | 5/2010 |
| WO | WO-2011027128 A1 | 3/2011 |
| WO | WO-2015070256 A1 | 5/2015 |

OTHER PUBLICATIONS

Glinsky et al, Clin. Exp. Metastasis, 1996, 14, 253-267.*
Glinsky et al, Cancer Research, 1996, 56, 5319-5324.*
Morrison et al, Gastroenterology, Apr. 2005, 128(4), supplement2, abstract S1915.*
Friend et al, J. Med. Chem. 1985, 28, 51-57.*
Wang, Doctoral Dissertation of the Fourth Medical University, 2007, pp. 1-129.*
Campieri et al, Gut, 1997, 41, 209-214.*
International Search Report and Written Opinion for International Application No. PCT/CN2018/081138, State Intellectual Property Office of the P. R. China, dated May 31, 2018, 11 pages (with English Translation).
Wang, Q., "Study on the oral colon-specific delivery system of 5-fluorouracil with the carrier: pectin," Doctoral Dissertation of the Fourth Military Medical University, School of Pharmacy, Department of Pharmacology, 129 pages (2007).
Sauraj, et al., "Synthesis and bio-evaluation of xylan-5-fluorouracil-1-acetic acid conjugates as prodrugs for colon cancer treatment," *Carbohydrate Polymers 157*:1442-1450, Elsevier, Netherlands (2017).
Yano, H., et al., "Prednisolone-appended alpha-cyclodextrin: alleviation of systemic adverse effect of prednisolone after intracolonic administration in 2,4,6-trinitrobenzenesulfonic acid-induced colitis rats," *Journal of Pharmaceutical Sciences 90*(12):2103-12, Elsevier, Netherlands (2001).
Zhou, J., et al., "The Investigation of a Prednisolone Prodrug for Colon-Specific Drug Delivery," *Pharmaceutical Journal of Chinese People's Liberation Army 17*(2):62-64, Jiefangjun Yaoxue Xuebao Bianjibu, China (2001).
Zhou, J., et al., "Colon-specific delivery release mechanism of prednisolone-dextran prodrug," *Chinese Pharmacological Bulletin 18*(3):328-330, Institute of Clinical Pharmacology, China (2002).
Bao, X., et al., "Roles of Dietary Amino Acids and Their Metabolites in Pathogenesis of Inflammatory Bowel Disease," *Mediators of Inflammation 2017*:1-9, Hindawi Publiaching Corporation, United States (Mar. 2017).
Friend, D. R., and Chang, G. W., "Drug glycosides: potential prodrugs for colon-specific drug delivery," *Journal of Medicinal Chemistry 28*(1):51-57, American Chemical Society, United States (Jan. 1985).
Glinsky, V. V., et al., "Intravascular metastic cancer cell homotypic aggregation at the sites of primary attachment to the endothelium," *Cancer Research 63*(13):3805-3811, American Association for Cancer Research, United States (Jul. 2003).
Lan, A., et al., "Acidic exgtracellular pH shifts colorectal cancer cell death from apoptosis to necrosis upon exposure to propionate and acetate, major end-products of the human probiotic propionibacteria," *Apoptosis 12*(3):573-591, Springer Netherlands, Netherlands (Dec. 2006).
Morrison, D., et al., "Delivery of short chain fatty acids to the colon," *Gastroenterology 128*(4_Suppl 2):A282, Abstract S1914, W.B. Saunders Ltd., United Kingdom (Apr. 2005).
Supplementary European Search Report and Search Opinion for EP Application No. EP 18 77 5995, The Hague, Netherlands, dated Dec. 7, 2020, 10 pages.
Examination Report No. 1 for AU Application No. 2018241798, Australia, dated Feb. 14, 2020, 2 pages.
Glinsky, G. V., et al., "Inhibition of Colony Formation in Agarose of Metastatic Human Breast Carcinoma and Melanoma Cells by Synthetic Glycoamine Analogs," *Clinical & Experimental Metastasis 14*(3):253-267, Rapid Science Publishers, United States (Jan. 1996).
Glinsky, G. V., et al., "Inhibition of Human Breast Cancer Metastasis in Nude Mice by Synthetic Glycoamines," *Cancer Research 56*:5319-5324, American Association for Cancer Research, United States (Dec. 1996).
Office Action for Chinese Application No. 201880005285.4, dated Nov. 12, 2021.
Acetic Acid Safety Data Sheet, "Acetic acid (glacial) 100% EMPROVE® EXPERT Ph Eur, BP, JP, USP," Sigma-Aldrich Co. LLC., accessed at https://www.sigmaaldrich.com/US/en/sds/sial/537020, Dec. 29, 2021, 11 pages.
Anaemetro® Pharmaceutical Interview Form, "Anaemetro® Intravenous Infusion: 500 mg," Pfizer Japan, Inc., Japan, revised 2018, accessed 2021 with appended Google Machine Translation, 166 pages.
Australian Government, Department of Health and Aging, "Australian Public Assessment Report for Prucalopride—Nov. 2011," Tga.gov.au, accessed at https://www.tga.gov.au/sites/default/files/auspar-resotrans.pdf, accessed on Jul. 22, 2022, 103 pages.
Bebet, L.Z., et al., "BDDCS Applied to Over 900 Drugs," AAPS J. 13(4):519-547, Springer Science+Business Media, Germany (2011).
Xu, S., et al., Experimental Methodology of Pharmacology, 3$^{rd}$ Edition (Chinese Edition), pp. 1863, People's Health Publishing House, Beijing, China, Jul. 1, 2010, 5 pages.
Otezla® Pharmaceutical Interview Form, "PDE4 Inhibitor—Otezla® tablets: 10 mg, 20 mg, 30 mg," Celgene Co., Ltd., revised Sep. 2019, accessed 2021 with appended Google Machine translation, 192 pages.

* cited by examiner

LACTULOSIDE COMPOUNDS AND PREPARATION AND USE THEREOF

CROSS-REFERENCE TO RELATED APPLICATIONS

This application is the National Stage of International Application No. PCT/CN2018/081138, filed Mar. 29, 2018, which claims the benefit of priority of Chinese Patent Application No. 201710205999.7, filed Mar. 30, 2017, the contents of both being incorporated by reference in their entirety for all purposes.

FIELD OF THE INVENTION

The present disclosure relates to the field of pharmaceutical chemistry, and particularly to a lactuloside compound having functions of colon-localized delivery and release, a preparation method and medical use thereof.

BACKGROUND OF THE INVENTION

Most of oral medicaments mainly enter systemic circulation via the absorption of upper gastrointestinal tract (such as stomach and small intestine) so as to exert therapeutic effects. For the diseases occurred in lower parts of gastrointestinal tract (such as cecum, colon and rectum), it is very difficult for medicaments to arrive at the lesion sites, and the medicaments only exert their efficacy depending on the drug concentration in the systemic circulation. Such colon diseases include inflammatory intestine diseases (such as ulcerative colitis and Crohn's disease), intestinal infection (such as intestinal amebiasis), intestinal cancer (such as colon cancer and rectal cancer), irritable bowel syndrome, chronic constipation, and so on. For the treatment of such diseases, most of the currently used common medicaments, such as glucocorticoids, non-steroidal anti-inflammatory drugs, immunomodulators, monoclonal antibodies, and wide-spectrum cytotoxic drugs, are administrated orally or via injection, and treat a localized disease through the systemic exposure amount of the drugs. Obvious disadvantage thereof is the unnecessary systemic side effect occurred when the drug treatment concentration is achieved at a localized site. For example, for the treatment of ulcerative colitis, using a glucocorticoid for the treatment will affect hypothalamus-pituitary-adrenal gland, and using an immunomodulator will result in abnormality and disorder of systemic immunity. The most ideal administration route is an administration at colon site, which can increase the localized drug concentration, and avoid or reduce the systemic exposure to a drug, thereby reducing the systemic side effect.

In order to solve the above problems, researchers have provided various technical solutions of colon-targeted drugs. For example, balsalazide releases an active drug, 5-aminosalicylic acid, to exert an anti-inflammatory effect under the action of azoreductase in colon flora. Mesalazine enema and budesonide enema are directly used for enema therapy at the end of the gastrointestinal tract (such as rectum and sigmoid colon). Colon-targeted formulations prepared by various complex formulating technologies have been reported. Furthermore, it has also been reported that it is desired to deliver a medicament to colon and then release an active drug with a prodrug technology by linking the active drug to a macromolecule carrier (such as glucan, xylan and cyclodextrin or the like). Reference can be made to the following literatures for details: Acta Pharmacologica Sinica, (2002), 18(3), 328-330; Pharmaceutical Journal of Chinese People's Liberation Army, (2001), 17(2), 62-64; Carbohydrate Polymers (2017), 157, 1442-1450; and Journal of Pharmaceutical Sciences (2001), 90(12), 2103-2112.

Therefore, at present, there is an urgent need for developing a simple, small molecule prodrug with unitary molecular structure and definite composition. The prodrug is obtained by linking an active drug to a small molecule carrier, and it cannot be absorbed by upper gastrointestinal tract or can be absorbed by upper gastrointestinal tract in very small amount, and cannot be degraded by endogenous enzymes. Most of the prodrug can be locally delivered to colon and rapidly release the active drug at colon site, thereby exerting efficacy and therapeutic effect.

SUMMARY OF THE INVENTION

The present disclosure is implemented in order to achieve the above object. In particular, the present disclosure discloses a class of lactuloside compounds, which can pass through the gastrointestinal tract of a mammal without being absorbed significantly by the gastrointestinal tract and hydrolyzed significantly by endogenous enzymes of a mammal host. Therefore, this kind of lactuloside compounds can arrive at the colon site of the mammal, and release an active drug at the colon under the action of colon flora. The lactuloside compound has a function of colon-localized drug release, and can be used for preventing or treating an intestinal disease Lactulose, also known as galactosylfructose, is a synthetic disaccharide obtained by bonding a galactose to a fructose via a β-1,4-glycosidic bond. Lactulose has a good *Bifidobacterium* multiplication function and an efficacy of modulating microecological balance of intestinal tract, and can be widely used in medical, food and animal feeding applications. Lactulose can find use in wide applications. It can reduce blood ammonia, purge, and treat constipation, and also can be used for preventing various liver diseases. It can also be used as low calorific value sweetener and functional food additive in foods. However, to date, it has not been reported to use lactulose as small molecule carrier to locally deliver an active drug.

According to an aspect of the disclosure, the present disclosure discloses a lactuloside prodrug compound represented by Formula (I) below:

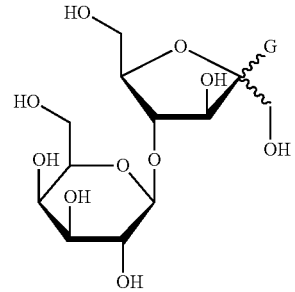

Formula (I)

wherein lactulosyl group is connected to a heteroatom of genin (G) via a glycosidic bond, the genin (G) is a group formed by removing one hydrogen atom from a heteroatom of an active pharmaceutical molecule, and "⁓" indicates that the lactulosyl group is connected to the heteroatom of the genin (G) via an α-glycosidic bond or a β-glycosidic bond.

Herein, "〰" indicates that the lactulosyl group is connected to the heteroatom of the genin (G) via an α-glycosidic bond or a β-glycosidic bond. That is, the lactuloside prodrug compound as formed has a structure represented by Formula (III) or (IV) below:

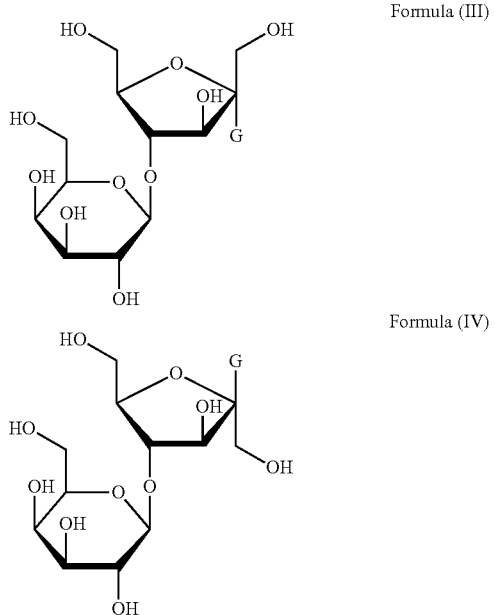

Formula (III)

Formula (IV)

Bonded via a α-glycosidic bond Bonded via an β-glycosidic bond

The lactuloside prodrug compound according to the present disclosure may be a compound bonded via an α-glycosidic bond, a compound bonded via a β-glycosidic bond, or a mixture of both.

According to the present disclosure, term "genin" has the common meaning in the art, that is, it represents a non-saccharide portion condensed with a saccharide in glycoside compounds.

The active drug according to the present disclosure is a chemical ingredient which has some pharmacological activity and is used for preventing or treating a human disease. The active drug may be a drug approved by various countries, or a candidate drug in human clinical trial phase.

According to the technical solutions of the present disclosure, the heteroatom is any one selected from a group consisting of oxygen atom, nitrogen atom and sulfur atom. The genin (G) is a group formed by removing one hydrogen atom from an alcoholic hydroxyl group, a phenolic hydroxyl group, an amino group, an amide group, or an NH group on a heterocycle of the active pharmaceutical molecule.

According to the technical contents of the present disclosure, the case where the genin is linked with two or more lactulosyl groups also falls within the scope of the present disclosure.

According to some embodiments of the present disclosure, the active pharmaceutical molecule is any one selected from a group consisting of glucocorticoids, apremilast, prucalopride, mesalamine, metronidazole, azathioprine, 6-mercaptopurine, 5-fluorouracil and tofacitinib The glucocorticoid is a general name of a class of synthetic drugs having similar functions with glucocorticoid secreted by adrenal cortex in human body. The glucocorticoids have functions of modulating biosynthesis and metabolism of saccharides, fats and proteins, as well as an anti-inflammatory effect. The glucocorticoids include not only the endogenous substances having the above characteristic and activity, but also many structure-optimized artificially synthesized drugs having similar structure and activity. Examples of the glucocorticoids include, but not limited to, cortisone acetate, prednisone, prednisone acetate, hydrocortisone, hydrocortisone acetate, hydrocortisone butyrate, hydrocortisone sodium succinate, hydrocortisone sodium phosphate, fludrocortisone, fludrocortisone acetate, prednisolone, prednisolone acetate, prednisolone sodium succinate, prednisolone sodium phosphate, betamethasone, betamethasone acetate, betamethasone dipropionate, clobetasone butyrate, betamethasone valerate, betamethasone sodium phosphate, beclomethasone dipropionate, mometasone furoate, clobetasol propionate, dexamethasone, dexamethasone acetate, dexamethasone sodium phosphate, paramethasone, fluticasone propionate, methylprednisolone, methylprednisolone acetate, fluorometholone, triamcinolone, triamcinolone acetonide, triamcinolone acetonide tert-butylacetate, fluocinolone acetonide, amcinonide, halcinonide, ciclesonide, budesonide, and deflazacort.

The glucocorticoid is preferably selected from a group consisting of hydrocortisone, prednisolone, methylprednisolone, dexamethasone, betamethasone, triamcinolone, and budesonide.

The active drug is more preferably selected from a group consisting of prednisolone, dexamethasone, budesonide, apremilast, prucalopride, and mesalamine.

In Formula (I) as shown above, the genin (G) is a group represented by Formula (II) below:

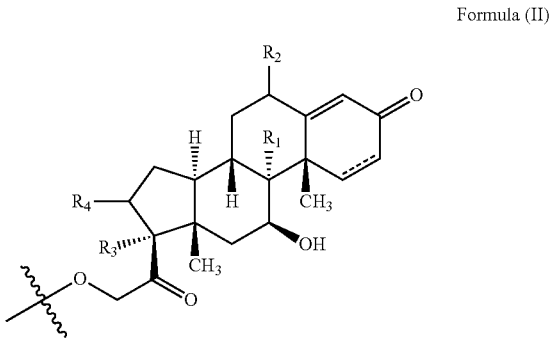

Formula (II)

wherein $R_1$ is H or F; $R_2$ is H, F or —$CH_3$; $R_3$ is —OH; and $R_4$ is H, —OH or —$CH_3$; or $R_3$ and $R_4$ are connected to form

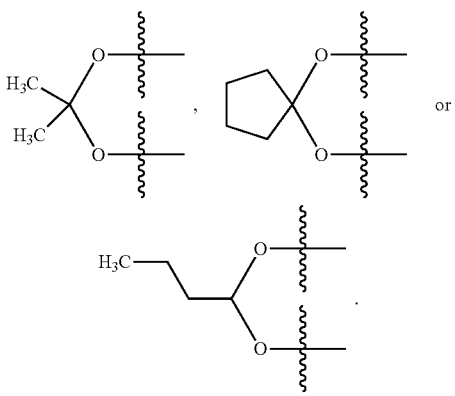

or

Preferably, the genin (G) is any one selected from a group consisting of:
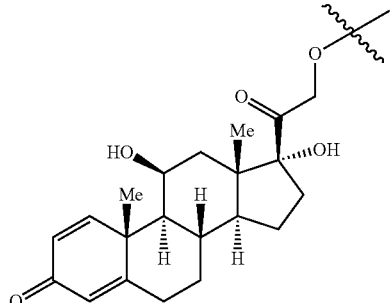
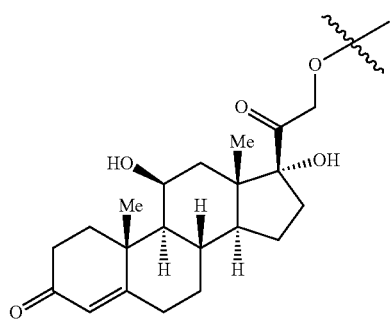
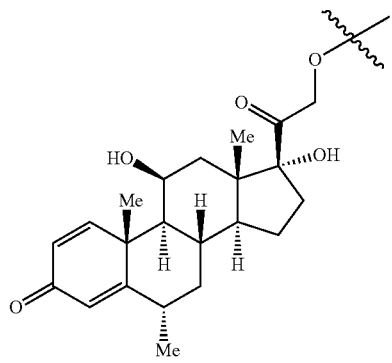
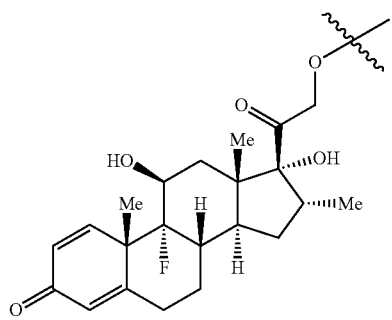
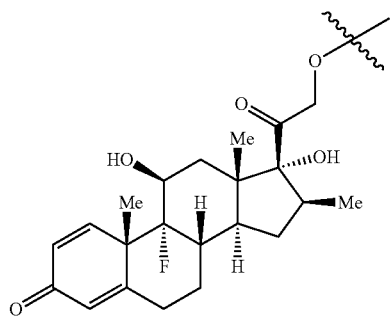
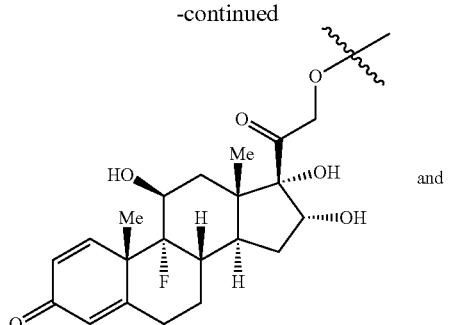
and
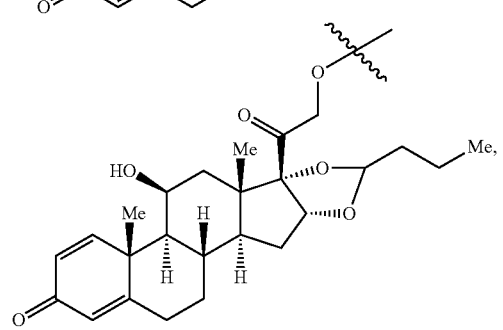
wherein Me represents —CH₃.
Further preferably, the genin (G) is any one selected from a group consisting of:
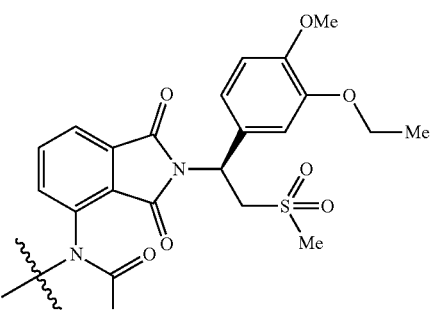
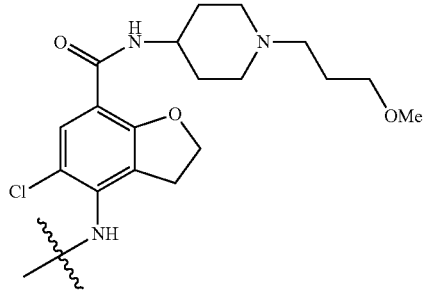
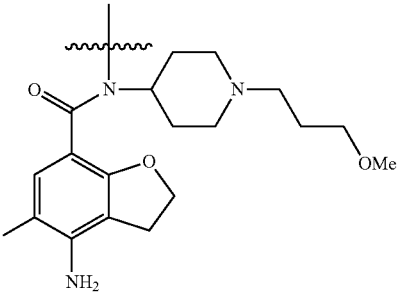

-continued

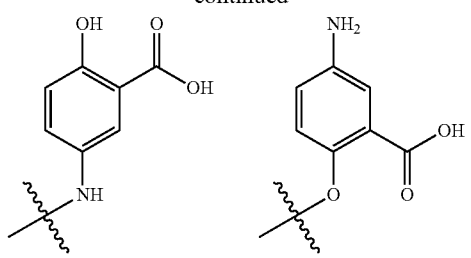

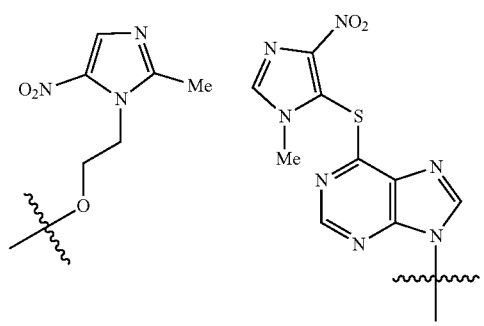

wherein Me represents —CH$_3$.

More preferably, the genin (G) is any one selected from a group consisting of:

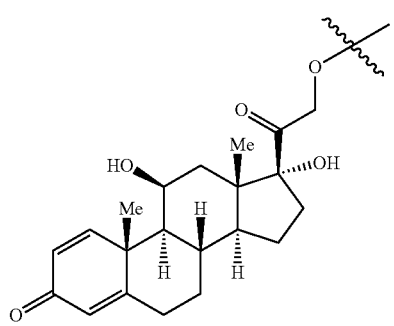

-continued

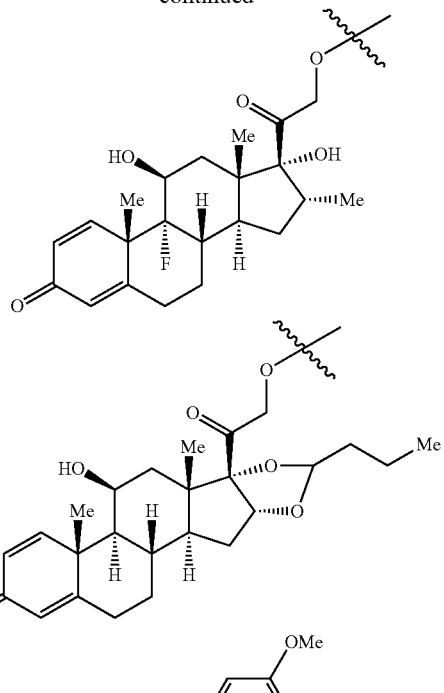

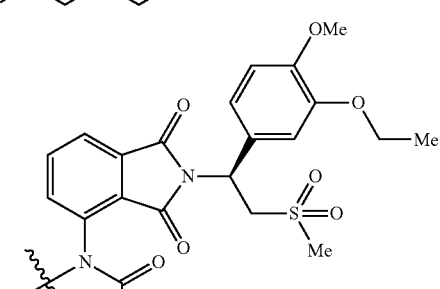

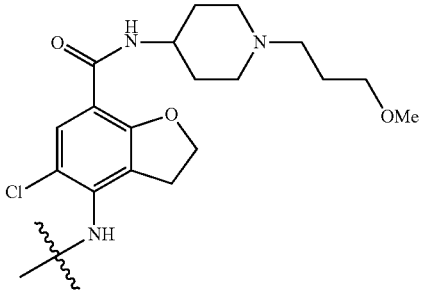

wherein Me represents —CH$_3$.

More specifically, the compound is any one selected from a group consisting of: (11β)-11,17-dihydroxyl-21-{[4-O-(β-D-galactopyranosyl)-D-fructofuranosyl]oxy}pregna-1,4-diene-3,20-dione;

(11β)-11,17-dihydroxyl-21-{[4-O-(β-D-galactopyranosyl)-D-fructofuranosyl]oxy}pregna-4-ene-3,20-dione;

(6α,11β)-11,17-dihydroxyl-6-methyl-21-{[4-O-(β-D-galactopyranosyl)-D-fructofuranosyl]oxy}pregna-1,4-diene-3,20-dione;

(11β,16α)-9-fluoro-11,17-dihydroxyl-16-methyl-21-{[4-O-(β-D-galactopyranosyl)-D-fructofuranosyl]oxy}pregna-1,4-diene-3,20-dione;

(11β,16β)-9-fluoro-11,17-dihydroxyl-16-methyl-21-{[4-O-(β-D-galactopyranosyl)-D-fructofuranosyl]oxy}pregna-1,4-diene-3,20-dione;

(11β,16α)-9-fluoro-11,16,17-trihydroxyl-21-{[4-O-(β-D-galactopyranosyl)-D-fructofuranosyl]oxy}pregna-1,4-diene-3,20-dione;

(11β,16α)-11-hydroxyl-16,17-(butylidenedioxy)-21-{[4-O-(β-D-galactopyranosyl)-D-fructofuranosyl]oxy}pregna-1,4-diene-3,20-dione;

2-methyl-5-nitro-1-{2-{[4-O-(β-D-galactopyranosyl)-D-fructofuranosyl]oxy}ethyl}imidazole;

6-[(1-methyl-4-nitro-1H-imidazol-5-yl)thio]-9-[4-O-(β-D-galactopyranosyl)-D-fructofuranosyl]-9H-purine;

6-thio-9-[4-O-(β-D-galactopyranosyl)-D-fructofuranosyl]-9H-purine;

5-fluoro-1-[4-O-(β-D-galactopyranosyl)-D-fructofuranosyl]pyrimidine-2,4(1H,3H)-dione;

N-{2-[(S)-1-(3-ethoxy-4-methoxyphenyl)-2-(methylsulfonyl)ethyl]-1,3-dioxo-2,3-dihydro-1H-isoindol-4-yl}-N'-[4-O-(β-D-galactopyranosyl)-D-fructofuranosyl]acetamide;

4-amino-5-chloro-2,3-dihydro-N-[1-(3-methoxypropyl)-4-piperidinyl]-N'-[4-O-(β-D-galactopyranosyl)-D-fructofuranosyl]-7-benzofurancarboxamide;

5-chloro-2,3-dihydro-4-{[4-O-(β-D-galactopyranosyl)-D-fructofuranosyl]amino}-N-[1-(3-methoxypropyl)-4-piperidinyl]-7-benzofurancarboxamide;

5-amino-2-{[4-O-(β-D-galactopyranosyl)-D-fructofuranosyl]oxy}benzoic acid;

2-hydroxyl-5-{[4-O-(β-D-galactopyranosyl)-D-fructofuranosyl]amino}benzoic acid;

17-hydroxyl-21-{[4-O-(β-D-galactopyranosyl)-D-fructofuranosyl]oxy}pregna-1,4-diene-3,11,20-trione; and 6-{N-methyl-N'-[(3R,4R)-4-methyl-1-(2-cyanoacetyl)piperidin-3-yl]amino}9-[4-O-(β-D-galactopyranosyl)-D-fructofuranosyl]-9H-purine.

According to a second aspect of the disclosure, the present invention disclosure provides a pharmaceutical composition comprising the lactuloside prodrug compound as described above and a pharmaceutically acceptable carrier.

According to a third aspect, the present invention disclosure provides use of the compound as described above in preparing a medicament for preventing or treating an intestinal disease, wherein the intestinal disease is selected from a group consisting of ulcerative colitis, Crohn's disease, infectious colitis, irritable bowel syndrome, chronic constipation, intestinal amebiasis, colon cancer, and rectal cancer, and more preferably, selected from a group consisting of ulcerative colitis, Crohn's disease and chronic constipation.

As demonstrated by the following examples, the lactuloside compound according to the present disclosure can pass through the gastrointestinal tract of a mammal without being absorbed significantly by the gastrointestinal tract and hydrolyzed significantly by endogenous enzymes of a mammal host. Therefore, the lactuloside compound can arrive at the colon site of the mammal, and release an active drug at the colon under the action of colon flora. The lactuloside compound has a function of colon-localized drug release, and can be used for preventing or treating an intestinal disease.

BRIEF DESCRIPTION OF THE DRAWINGS

Drawings are provided below to describe the embodiments according to the present disclosure in detail, in which.

DETAILED DESCRIPTION OF THE INVENTION

Figure 1:
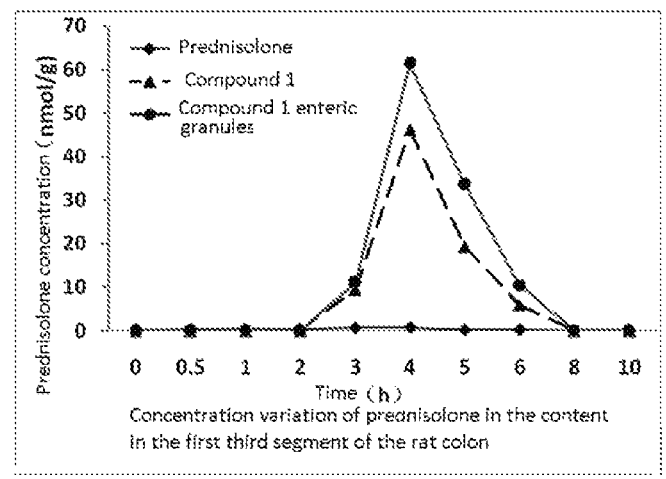
FIG. 1 shows the concentration variation of prednisolone in the content in the first third (including cecum) of the colon of a rat after intragastric administration.

Specifically, the example compounds provided in the present disclosure have structures as shown in Table 1 below.

TABLE 1
| Compound | Chemical Name | Chemical Structure |
| --- | --- | --- |
| 1 | (11β)-11,17-dihydroxyl-21-{[4-O-(β-D-galactopyranosyl)-D-fructofuranosyl]oxy}pregna-1,4-diene-3,20-dione | 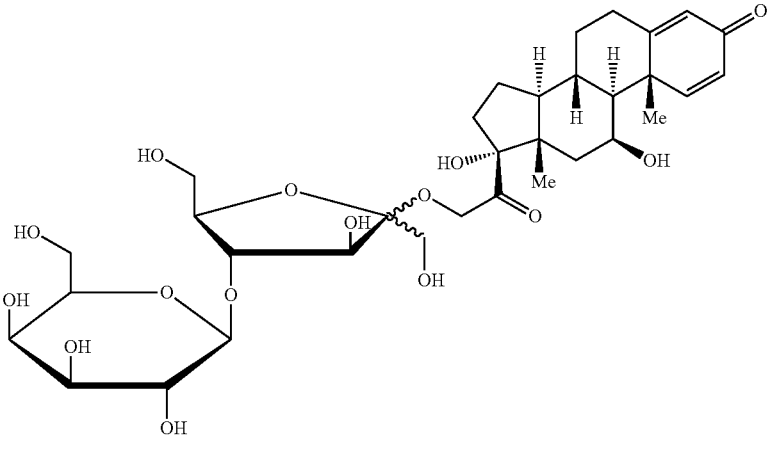 |
| 2 | (11β)-11,17-dihydroxyl-21-{[4-O-(β-D-galactopyranosyl)-D-fructofuranosyl]oxy}pregna-4-ene-3,20-dione | 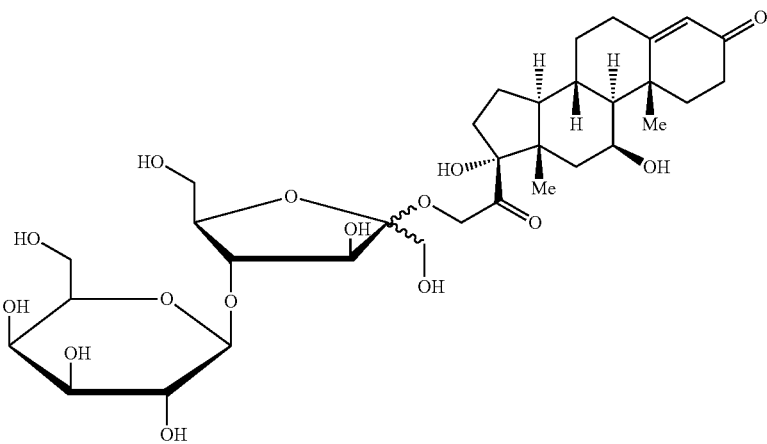 |
| 3 | (6α,11β)-11,17-dihydroxyl-6-methyl-21-{[4-O-(β-D-galactopyranosyl)-D-fructofuranosyl]oxy}pregna-1,4-diene-3,20-dione | 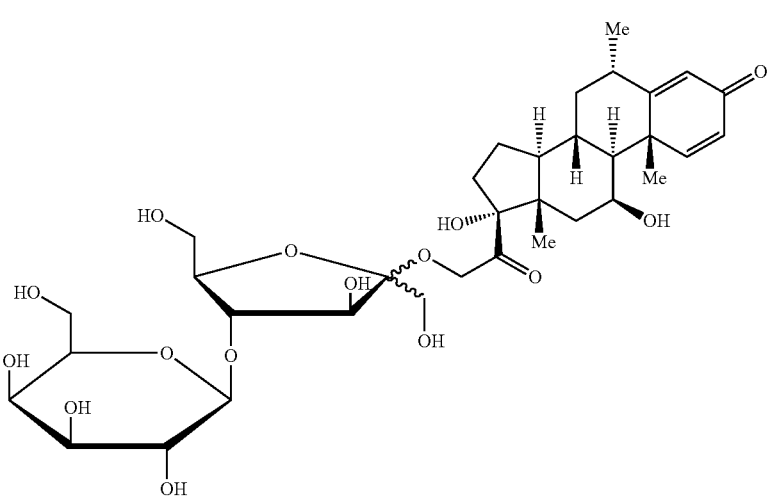 |

TABLE 1-continued
| Compound | Chemical Name | Chemical Structure |
|---|---|---|
| 4 | (11β,16α)-9-fluoro-11,17-dihydroxyl-16-methyl-21-{[4-O-(β-D-galactopyranosyl)-D-fructofuranosyl]oxy}pregna-1,4-diene-3,20-dione | 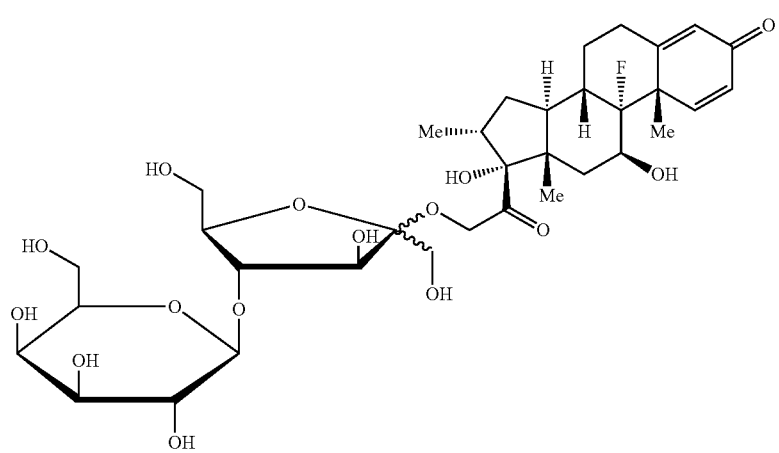 |
| 5 | (11β,16β)-9-fluoro-11,17-dihydroxyl-16-methyl-21-{[4-O-(β-D-galactopyranosyl)-D-fructofuranosyl]oxy}pregna-1,4-diene-3,20-dione | 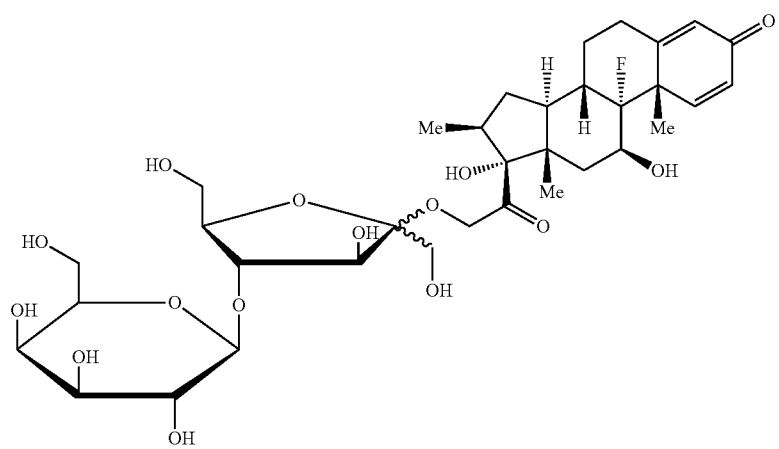 |
| 6 | (11β,16α)-9-fluoro-11,16,17-trihydroxyl-2-1-{[4-O-(β-D-galactopyranosyl)-D-fructofuranosyl]oxy}pregna-1,4-diene-3,20-dione | 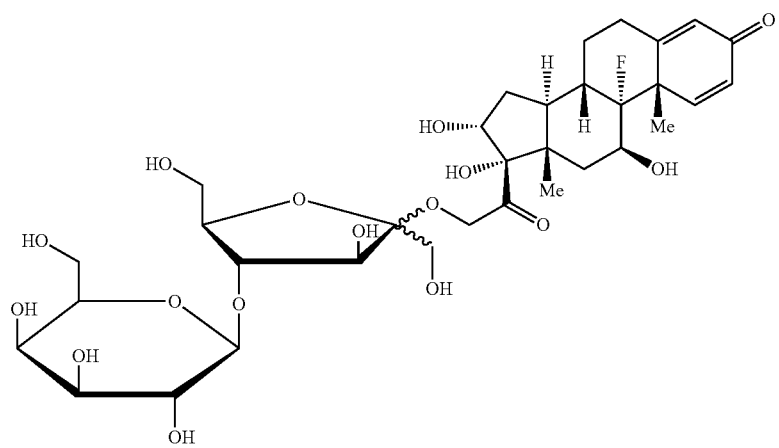 |

TABLE 1-continued

| Compound | Chemical Name | Chemical Structure |
|---|---|---|
| 7 | (11β,16α)-11-hydroxyl-16,17-(butylidenedioxy)-21-{[4-O-(β-D-galactopyranosyl)-D-fructofuranosyl]oxy}pregna-1,4-diene-3,20-dione | 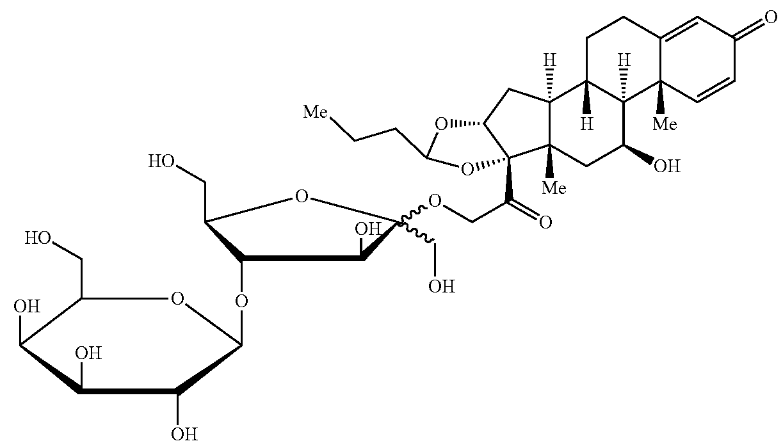 |
| 8 | 2-methyl-5-nitro-1-{2-{[4-O-(β-D-galactopyranosyl)-D-fructofuranosyl]oxy}ethyl}imidazole | 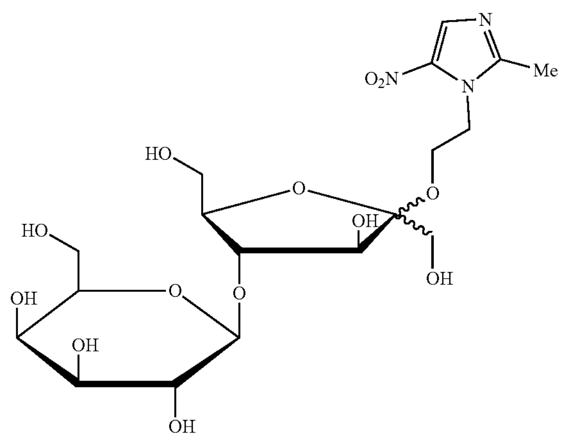 |
| 9 | 6-[(1-methyl-4-nitro-1H-imidazol-5-yl)thio]-9-[4-O-(β-D-galactopyranosyl)-D-fructofuranosyl]-9H-purine | 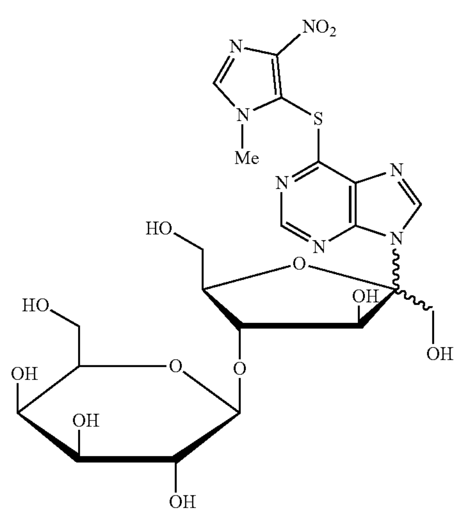 |

TABLE 1-continued

| Compound | Chemical Name | Chemical Structure |
|---|---|---|
| 10 | 6-thio-9-[4-O-(β-D-galactopyranosyl)-D-fructofuranosyl]-9H-purine | 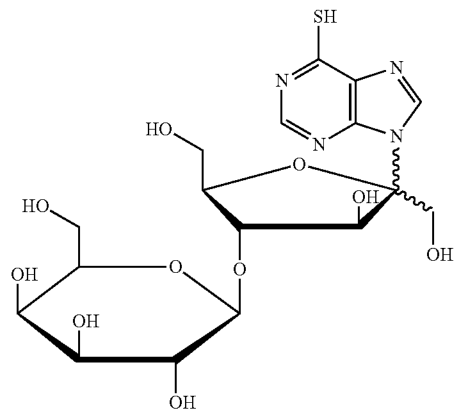 |
| 11 | 5-fluoro-1-[4-O-(β-D-galactopyranosyl)-D-fructofuranosyl]pyrimidine-2,4(1H,3H)-dione | 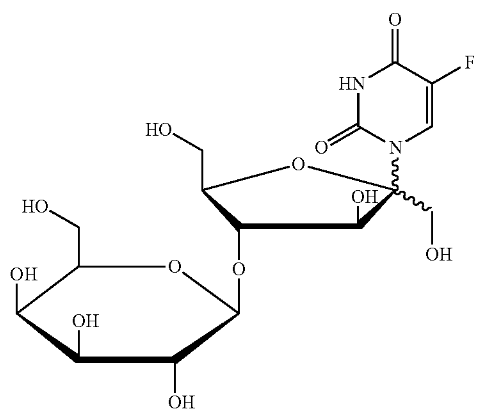 |
| 12 | N-{2-[(S)-1-(3-ethoxy-4-methoxyphenyl)-2-(methylsulfonyl)ethyl]-1,3-dioxo-2,3-dihydro-1H-isoindol-4-yl}-N'-[4-O-(β-D-galactopyranosyl)-D-fructofuranosyl]acetamide | 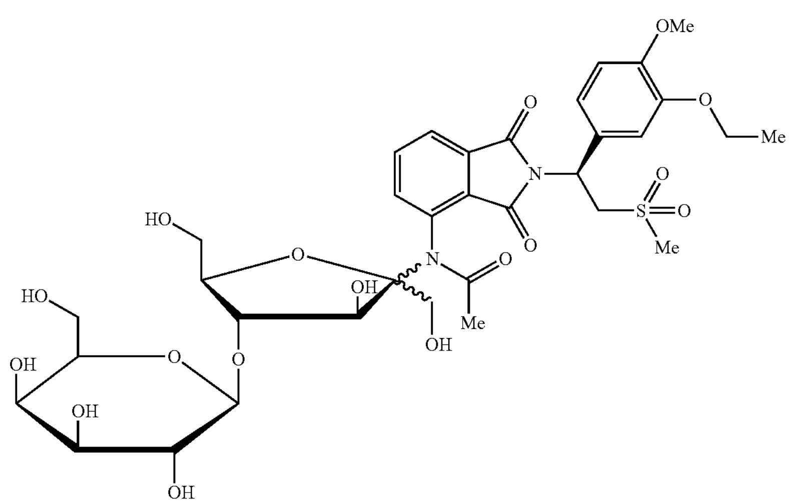 |

TABLE 1-continued

| Compound | Chemical Name | Chemical Structure |
|---|---|---|
| 13 | 4-amino-5-chloro-2,3-dihydro-N-[1-(3-methoxypropyl)-4-piperidinyl]-N'-[4-O-(β-D-galactopyranosyl)-D-fructofuranosyl]-7-benzofurancarboxamide | 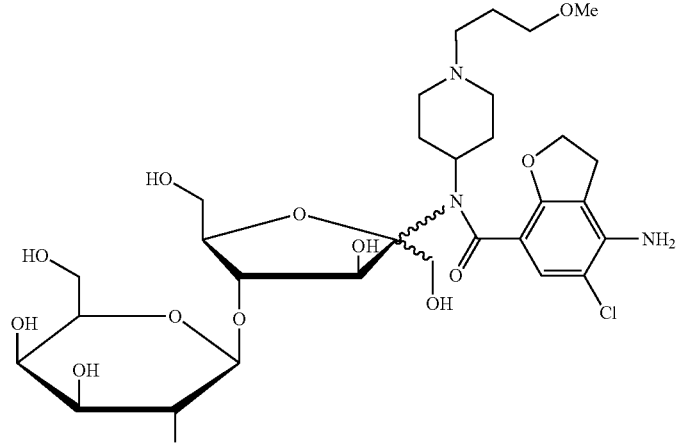 |
| 14 | 5-chloro-2,3-dihydro-4-{[4-O-(β-D-galactopyranosyl)-D-fructofuranosyl]amino}-N-[1-(3-methoxypropyl)-4-piperidinyl]-7-benzofurancarboxamide | 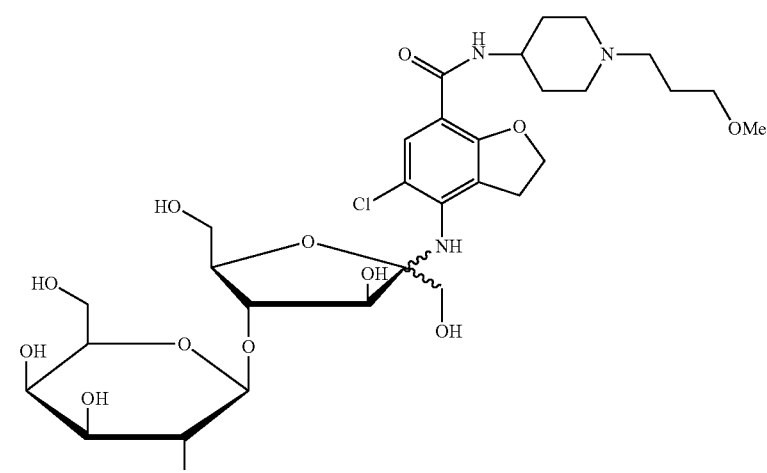 |
| 15 | 5-amino-2-{[4-O-(β-D-galactopyranosyl)-D-fructofuranosyl]oxy}benzoic acid | 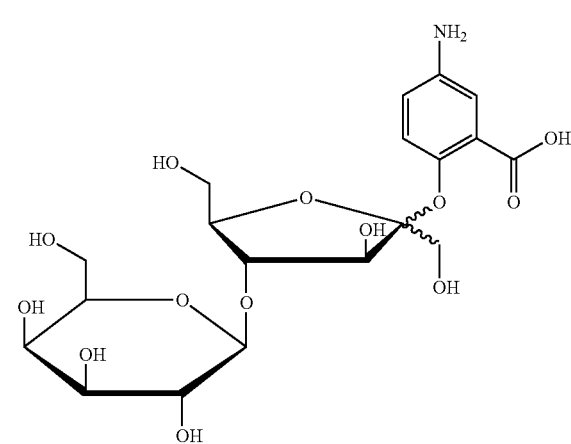 |

TABLE 1-continued

| Compound | Chemical Name | Chemical Structure |
|---|---|---|
| 16 | 2-hydroxyl-5-{[4-O-(β-D-galactopyranosyl)-D-fructofuranosyl]amino}benzoic acid | 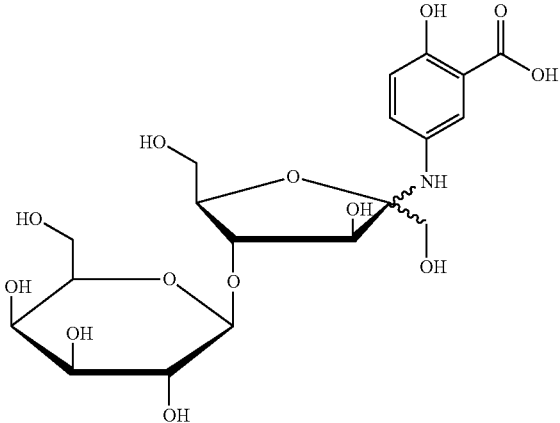 |
| 17 | 17-hydroxyl-21-{[4-O-(β-D-galactopyranosyl)-D-fructofuranosyl]oxy}pregna-1,4-diene-3,11,20-trione | 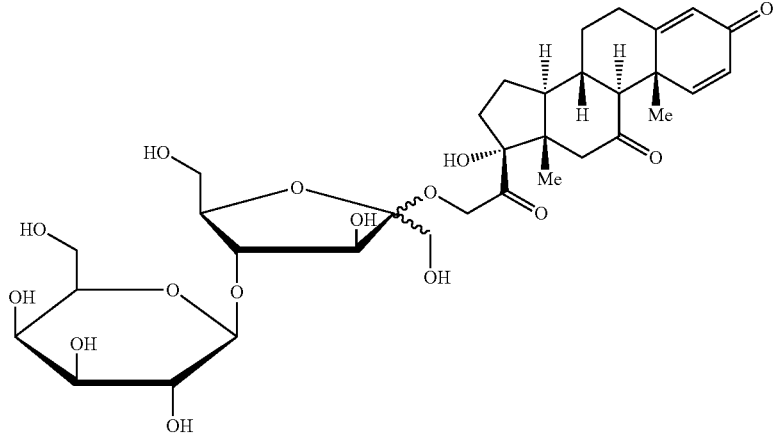 |
| 18 | 6-{N-methyl-N'-[(3R,4R)-4-methyl-1-(2-cyanoacetyl)piperidin-3-yl]amino}9-[4-O-(β-D-galactopyranosyl)-D-fructofuranosyl]-9H-purine | 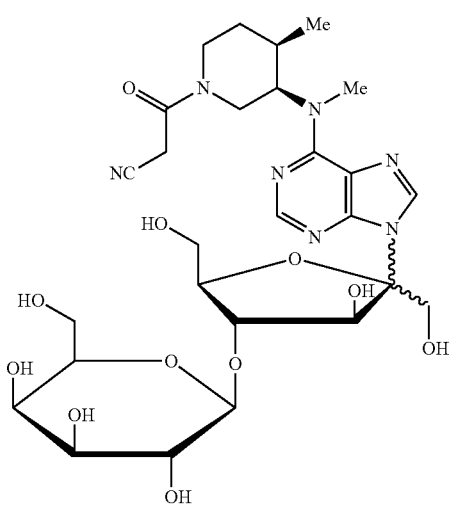 |

Next, the methods for preparing the compound of the present disclosure will be described.

The compound of the present disclosure may be prepared for example by the following preparation methods.

(Preparation Method A)
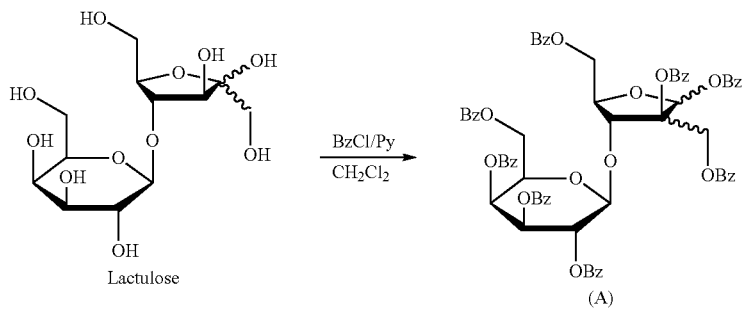
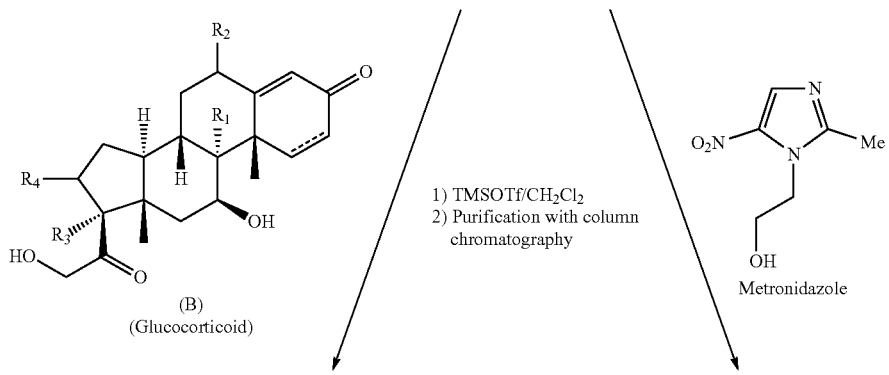
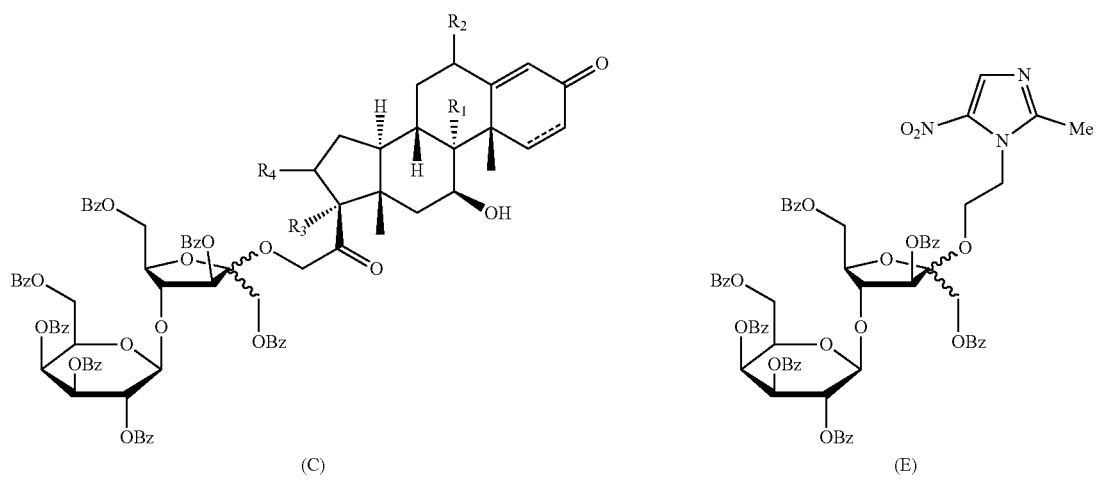

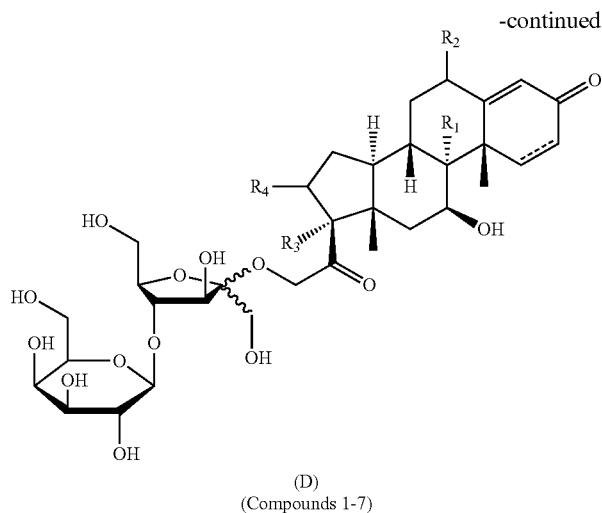

(D)
(Compounds 1-7)

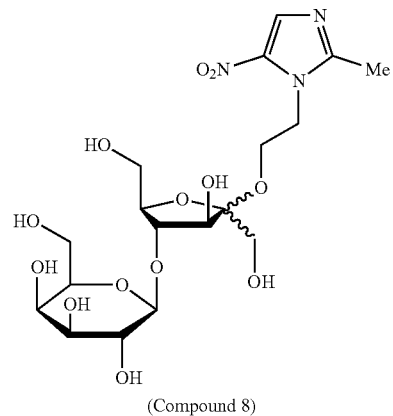

(Compound 8)

Lactulose is reacted with benzoyl chloride (BzCl) in a pyridine (Py) solvent in the presence of dichloromethane (CH$_2$Cl$_2$) to be fully acylated to obtain octa-benzoyl lactulose (A), which is then subjected to a glycosylation condensation reaction with a primary hydroxyl group at position 21 of a glucocorticoid drug (B) under the action of trimethylsilyl trifluoromethanesulfonate (TMSOTf). The reaction mixture is purified with column chromatography to obtain an intermediate (C), and then the benzoyl groups on the glycosyl group is removed with an ammonia methanol solution to obtain a target product (D). Typical examples of the target product (D) are Compounds 1 to 7 listed in the above table. Likewise, octa-benzoyl lactulose (A) is subjected to a glycosylation reaction with metronidazole, and then the benzoyl groups are removed to obtain a target compound 8. The corresponding target compounds may be prepared by using a pharmaceutical molecule with a primary hydroxyl group in the above method.

(Preparation Method B)

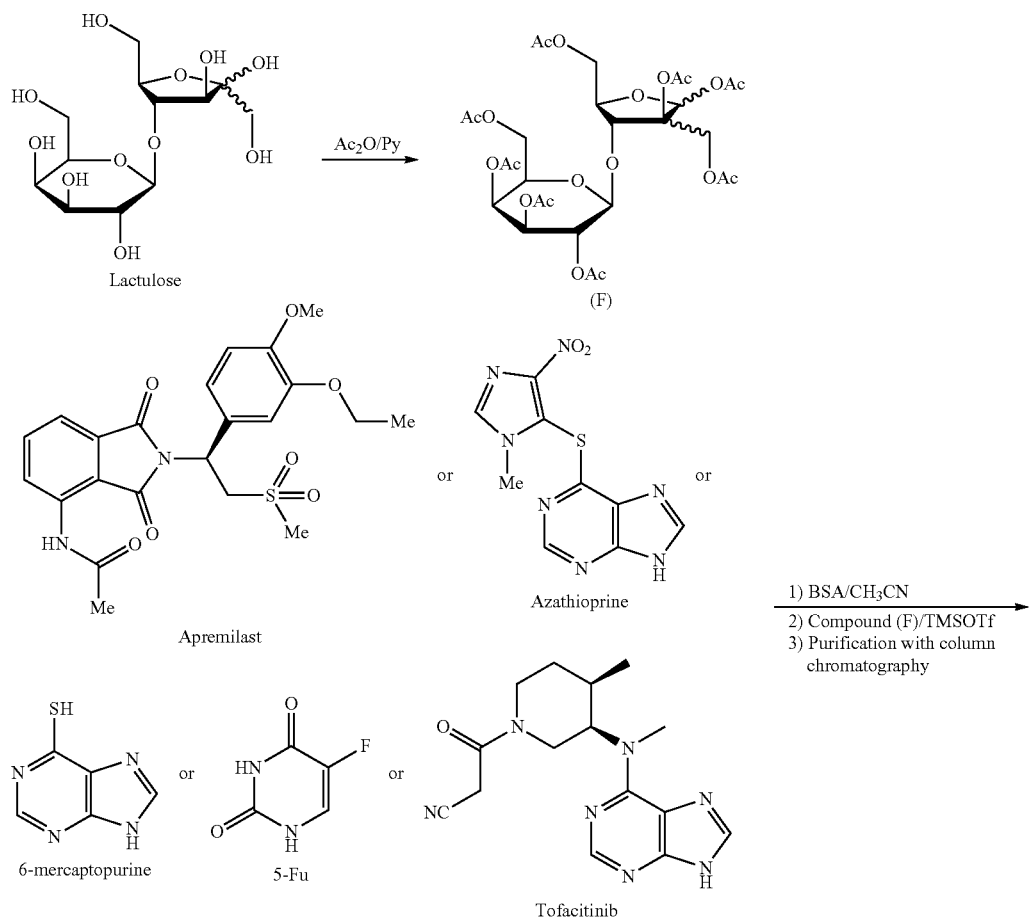

-continued
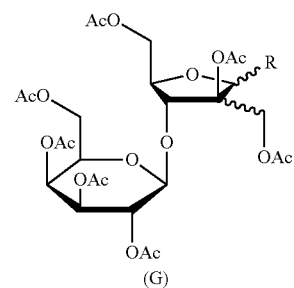
(G)
1) Alkaline hydrolysis
2) Purification
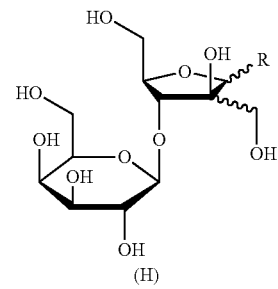
(H)
(Compounds 9-12 and 18)
Compound 9 R = 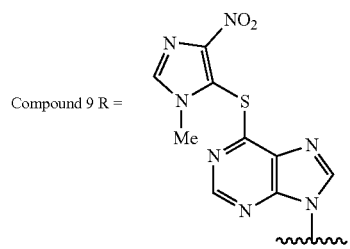
Compound 10 R = 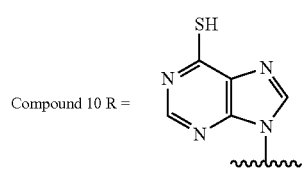
Compound 11 R = 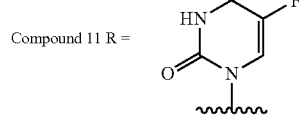
Compound 12 R = 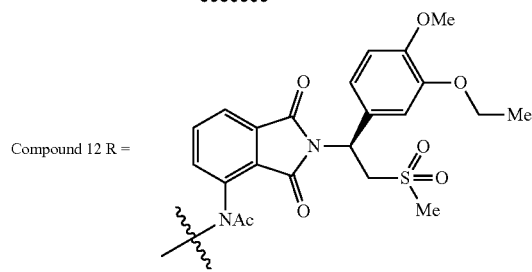

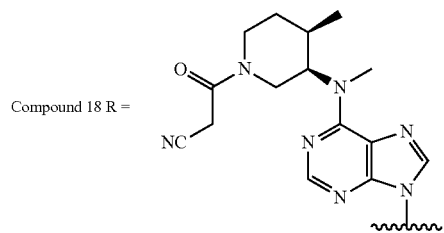

Compound 18 R =

All hydroxyl groups of lactulose are acetylated with acetic anhydride/pyridine to obtain octa-acetyl lactulose (Compound F).

Azathioprine, 6-mercaptopurine, 5-fluorouracil (5-Fu) or apremilast is silanized with N,O-bis(trimethylsilyl)acetamide (BSA) in an acetonitrile solvent, and then subjected to a glycosylation condensation reaction with octa-acetyl lactulose (F) under the action of trimethylsilyl trifluoromethanesulfonate (TMSOTf). The reaction mixture is purified with column chromatography to obtain an intermediate (G), which is then subjected to an alkaline treatment to remove the acetyl groups on the glycosyl group and preparatively purified to obtain a target compound (H) (Compounds 9, 10, 11 and 12).

A corresponding lactuloside compound (Compound 18) may be obtained from Tofacitinib by a synthesis method similar to the above method.

(Preparation Method C)

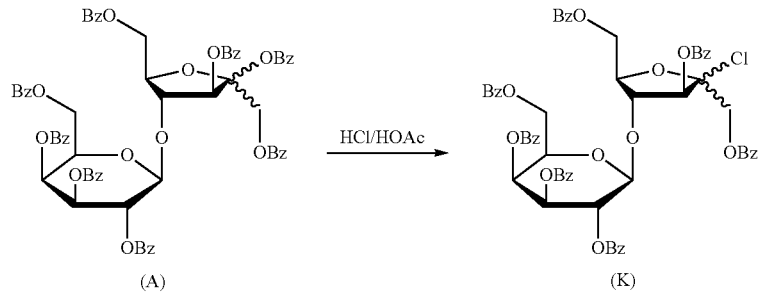

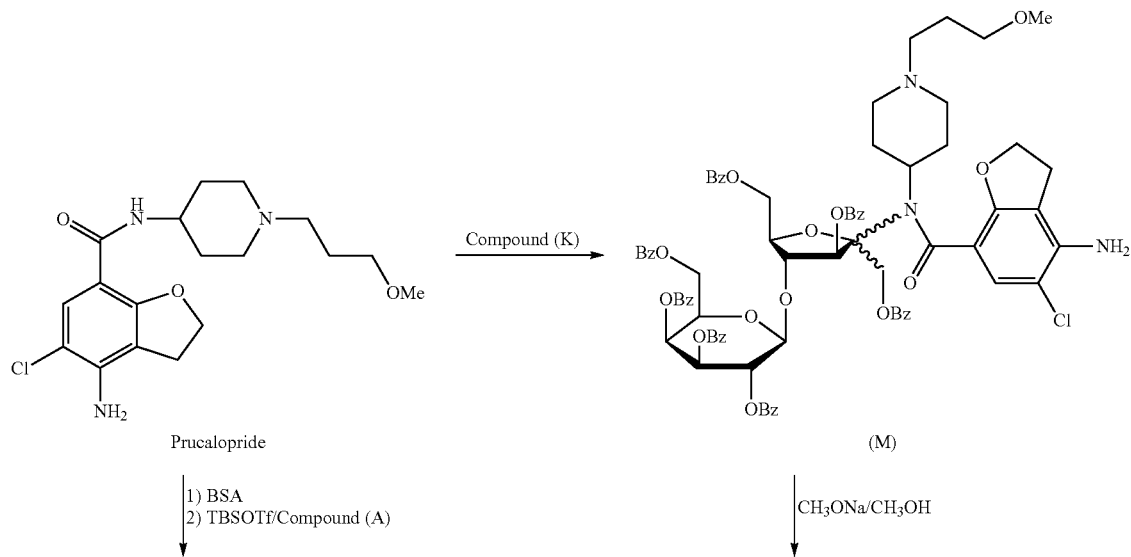

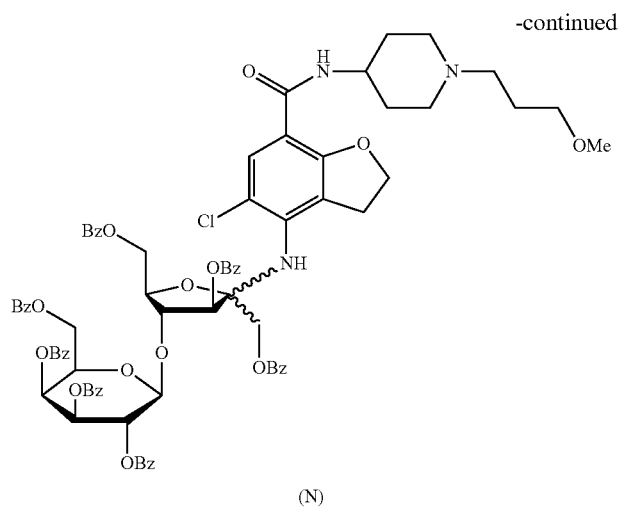

(N)

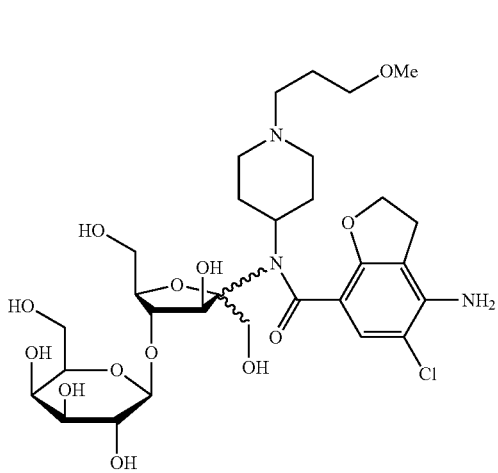

Compound 13

|CH₃ONa/CH₃OH
↓

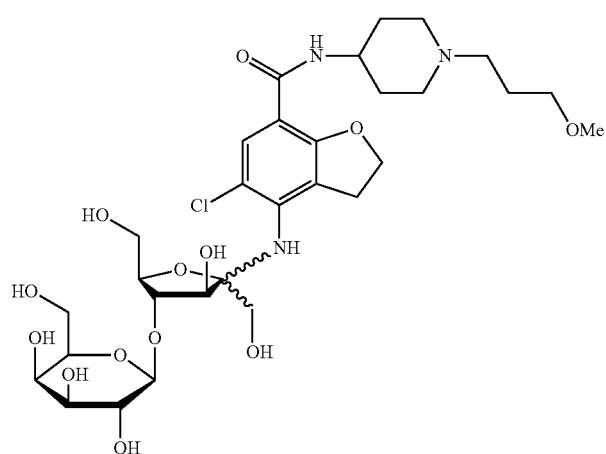

Compound 14

Octa-benzoyl lactulose (A) is converted into a chloride (K) with hydrogen chloride or hydrogen bromide. Prucalopride is reacted with the chloride (K) to produce an intermediate (M). The crude product is purified with column chromatography, then subjected to an alkaline treatment to remove the benzoyl groups on the glycosyl group and preparatively purified to obtain Compound 13.

Prucalopride is silanized with N,O-bis(trimethylsilyl)acetamide (BSA), and then subjected to a glycosylation condensation reaction with octa-benzoyl lactulose (A) under the action of tert-butyldimethylsilyl trifluoromethanesulfonate (TBSOTf). The reaction mixture is purified with column chromatography to obtain an intermediate (N), which is then subjected to an alkaline treatment to remove the benzoyl groups on the glycosyl group and preparatively purified to obtain Compound 14.

(Preparation Method D)

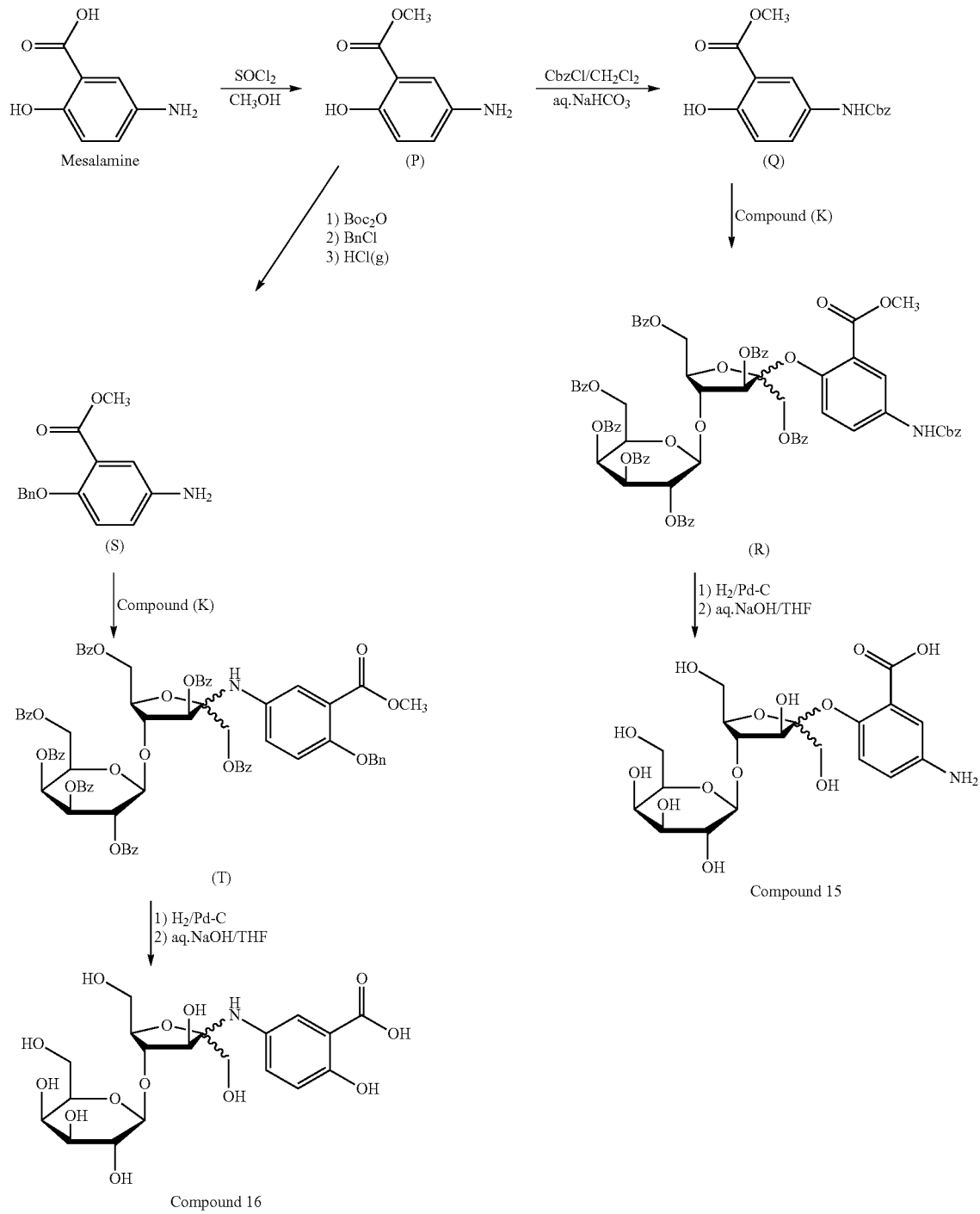

5-Aminosalicylic acid (mesalamine) is methyl-esterified to obtain mesalamine methyl ester (P), and then the amino group is protected with benzyl chloroformate to obtain Compound (Q). The phenolic hydroxyl group of Compound (Q) is subjected to a glycosylation reaction with the saccharide chloride (K) to obtain mesalamine O-glycoside compound (R). Finally the benzyloxy carbonyl groups are removed by hydrogenation and the methyl ester and the benzoate are removed with an alkaline solution to obtain Compound 15.

After the amino group of mesalamine methyl ester (P) is protected with di-tert-butyl dicarbonate ($Boc_2O$), the phenolic hydroxyl group is protected by reaction with benzyl chloride, and then the Boc protection group is removed to obtain Compound (S). The amino group of Compound (S) is subjected to a glycosylation reaction with the saccharide chloride (K) to obtain mesalamine N-glycoside compound (T). Finally the benzyl groups are removed by hydrogenation and the methyl ester and the benzoate are removed with an alkaline solution to obtain Compound 16.

The compound of Formula (I) of the present disclosure may be mixed with a pharmaceutically acceptable carrier to prepare various oral pharmaceutical compositions. The compound of Formula (I) can be mixed with acceptable and common auxiliary additives such as disintegrant, excipient, lubricant, binder, and filler or the like, and formulated into an oral medicament of solid preparation, such as tablet, pill, capsule or various corresponding sustained release preparation or control release preparation, by a convention method. Alternatively, the compound of Formula (I) can be mixed with a surfactant such as solubilizer, emusifier, wetting agent, foaming agent or defoaming agent, diluent, preservative, stabilizer, flavoring agent, thickener, or the like, and formulated into an oral medicament of liquid preparation, such as aqueous preparation and syrup or the like.

The present disclosure further provides the methods of in vitro stability test, drug metabolism, and pharmacodynamic test of the example compounds. The results demonstrate that the compound of the present disclosure has a good colon-localized drug release function and an advantage of treating intestinal diseases, and is especially suitable for drug therapy at cecum and colon sites.

Therefore, the present disclosure further provides use of the compound of Formula (I) in preparing a pharmaceutical composition for preventing or treating an intestinal disease or condition, wherein the intestinal disease or condition is selected from a group consisting of ulcerative colitis, Crohn's disease, infectious colitis, irritable bowel syndrome, chronic constipation, intestinal amebiasis, colon cancer, and rectal cancer.

The intestinal disease or condition is preferably selected from a group consisting of ulcerative colitis, Crohn's disease and chronic constipation.

EXAMPLES

The method for preparing the compound of the present disclosure will be illustrated in detail below by means of examples. It should be noted that the technical solutions of the present disclosure are not limited the examples.

In the examples below, lactulose was purchased from J&K Scientific (99.0%). Prednisone (99.0%), prednisolone (99%), hydrocortisone (98.8%), dexamethasone (98.8%), betamethasone (99.8%), triamcinolone (99.0%), and budesonide (98.5%) were purchased from Shandong Taihua Bio&Tech Co., Ltd. Methylprednisolone (98%) was purchased from Wuhan Dongkang Source Technology Co., Ltd. Metronidazole (98.0%) was purchased from Saen Chemical Technology Co., Ltd. Azathioprine (98%) was purchased from Aladdin Reagent. 6-Mercaptopurine (98.0%) and 5-fluorouracil (98.0%) were purchased from Shanghai Bide Pharma Tech Co., Ltd. Apremilast (98.0%) was purchased from Adamas Reagent Co., Ltd. Prucalopride (99.2%) was purchased from Zhiwei Chemical Technology Co., Ltd. Mesalamine (99.7%) was purchased from Hubei Prosperity Galaxy Chemical Co., Ltd.

In the present application, all other used reagents are commercially available unless specifically indicated otherwise.

In addition, in the specification, "%" means % by weight unless specifically indicated otherwise.

Preparation Example 1

(11β)-11,17-dihydroxyl-21-{[4-O-(β-D-galactopyranosyl)-D-fructofuranosyl]oxy}pregna-1,4-diene-3, 20-dione (Compound 1)

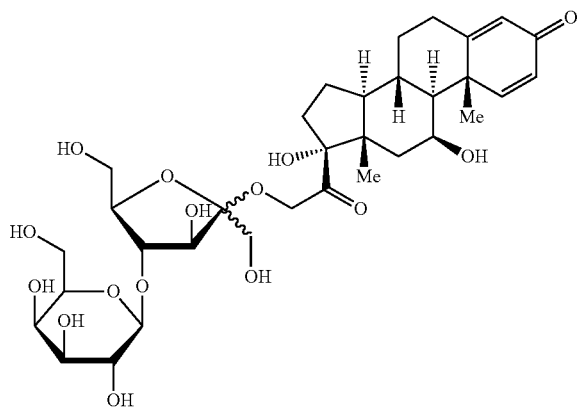

Step I:

Lactulose (10 g, 0.029 mol) was dissolved in 100 ml pyridine, and 60 ml dichloromethane was added thereto. The mixture was stirred and cooled to 0° C. Benzoyl chloride (61.1 g, 0.435 mol) was added dropwise. After that, the mixture was warmed to room temperature and reacted for 16 hours.

The reaction solution was concentrated to dryness under reduced pressure. The residue was dissolved in 200 ml dichloromethane, and washed sequentially with a citric acid solution (pH>4) (120 ml, 3 times), a saturated sodium bicarbonate solution (120 ml, once), and a saturated sodium chloride solution (20 ml, once). The organic phase was dried over anhydrous sodium sulfate for 30 minutes, and filtered. The filtrate was concentrated under reduced pressure, and then purified with column chromatography to obtain 30.0 g of a white solid, i.e., the product of Step I (Compound A), at a yield of 87.2%. ESI(+) m/z: 1192.3 [M+NH$_4$]$^+$ 1197.2 [M+Na]$^+$ Step II:

Under the protection of argon, the above product of Step I (10.1 g, 8.59 mmol) and prednisolone (2.6 g, 7.16 mmol) were dissolved in 400 ml dichloromethane, and 5 g of 4 Å molecular sieve was added thereto. The mixture was stirred and cooled to −35° C. TMSOTf (2.7 g, 12.2 mmol) was added dropwise. The reaction temperature was kept for 2 hours, and then increased to −15° C., and the reaction was performed for 2 to 3 hours.

Trimethyl pyridine (2.2 g, 17.9 mmol) was added dropwise to the reaction mixture. The resultant mixture was warmed to 25° C. and stirred for 1 hour. Then, the reaction solution was washed sequentially with a citric acid solution (pH>4) (200 ml, 3 times), a saturated sodium carbonate solution (200 ml, once), and a saturated sodium chloride solution (200 ml, once). The organic phase was dried over anhydrous sodium sulfate for 30 minutes, and filtered. The filtrate was concentrated, and then purified with column chromatography to obtain 7.5 g of a white solid, i.e., the product of Step II, at a yield of 61.5%. ESI(+) m/z: 1435.2 [M+Na]+

Step III: Preparation of Compound 1

The above product of Step II (5.4 g, 3.8 mmol) was dissolved in 10 ml tetrahydrofuran, and 40 ml ammonia methanol (10 M) was added thereto. The mixture was stirred at room temperature for 72 hours.

The reaction solution was concentrated to dryness under reduced pressure. The residue was dissolved in water, and then the solution was concentrated to dryness. This procedure was repeated three times. 30 ml water and 10 ml methyl tert-butyl ether were added to the residue. After the residue was dissolved, the solution was separated. The aqueous phase was concentrated under reduced pressure, and the remaining water was taken away by anhydrous ethanol. The resultant solid was suspended in 30 ml acetone. The suspension was stirred for 50 minutes and then filtered. The filter cake was drip washed with acetone, and evacuated to dryness. Then, the filter cake was recrystallized in methanol/water (v/v=1/1) for purification, to obtain 1.5 g of a white solid, i.e., the title compound (Compound 1), at a yield of 57.7%. ESI(+) m/z: 707.4 [M+Na]$^+$.

$^1$H-NMR (DMSO-d6, 500M, BRUKER AV-500): δ (ppm) 7.32 (1H, d, =CH), 6.19 (1H, dd, J$_1$=1.5 Hz, J$_2$=10 Hz, =CH), 5.91 (1H, s, =CH), 5.23 (1H, s, CH(O)$_2$—), 5.09 (1H, d, O—CH$_2$—CO—), 4.82-4.79 (1H, t), 4.74-4.71 (2H, m), 4.69 (1H, d, O—CH$_2$—CO—), 4.62 (1H, s), 4.53 (1H, d), 4.38 (1H, d), 4.29-4.23 (3H, m), 4.14-4.10 (2H, m), 3.84-3.81 (1H, m), 3.78-3.75 (1H, m), 3.61-3.59 (2H, m), 3.56-3.48 (3H, m), 3.46-3.42 (1H, m), 3.40-3.36 (2H, m), 3.32-3.30 (2H, m), 2.56-2.53 (2H, m), 2.30-2.28 (1H, m), 2.04-2.02 (2H, m), 1.89-1.85 (1H, dd, J$_1$=3 Hz, J$_2$=13.5 Hz), 1.66-1.60 (3H, m), 1.41-1.39 (1H, m), 1.38 (3H, s, —CH$_3$), 1.30-1.23 (1H, m), 1.02-0.99 (1H, m), 0.91-0.88 (1H, dd, J$_1$=3 Hz, J$_2$=10.5 Hz), 0.779 (3H, s, —CH$_3$).

Preparation Example 2

(11β)-11,17-dihydroxyl-21-{[4-O-(β-D-galactopyranosyl)-D-fructofuranosyl]oxy}pregna-4-ene-3,20-dione (Compound 2)

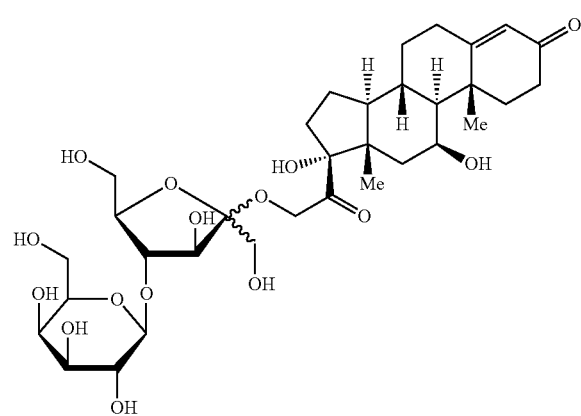

The Preparation Example 2 is implemented in a way similar to the Preparation Example 1 except that prednisolone is replaced by hydrocortisone, obtaining 0.45 g of the title compound. ESI(+) m/z: 709.3 [M+Na]$^+$.

$^1$H-NMR (DMSO-d6, 400M, BRUKER AV-400): δ (ppm) 5.56 (1H, s, =CH), 5.29 (1H, s), 5.16 (1H, d), 4.87-4.78 (5H, m), 4.68-4.63 (1H, m), 4.46 (1H, m), 4.35-4.34 (1H, m), 4.29-4.22 (3H, m), 4.18-4.11 (2H, m), 3.82-3.80 (1H, m), 3.77-3.74 (1H, m), 3.59 (2H, m), 3.56-3.42 (4H, m), 3.40-3.34 (2H, m), 3.30 (2H, m), 2.57-2.54 (1H, m), 2.45-2.34 (2H, m), 2.21-2.17 (2H, m), 2.10-2.07 (1H, m), 1.93-1.88 (3H, m), 1.81-1.75 (1H, m), 1.66-1.55 (3H, m), 1.42-1.40 (1H, m), 1.36 (3H, s, —CH$_3$), 1.28-1.24 (1H, m), 1.06-0.98 (1H, m), 0.88-0.85 (1H, d), 0.75 (3H, s, —CH$_3$).

Preparation Example 3

(6α,11β)-11,17-dihydroxyl-6-methyl-21-{[4-O-(β-D-galactopyranosyl)-D-fructofuranosyl]oxy}pregna-1,4-diene-3,20-dione (Compound 3)

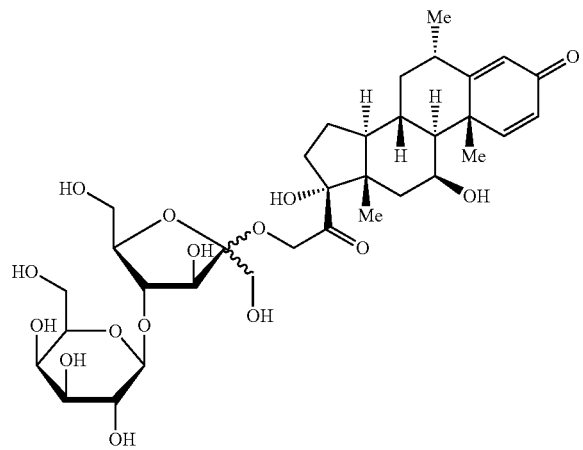

The Preparation Example 3 is implemented in a way similar to the Preparation

Example 1 except that prednisolone is replaced by methylprednisolone, obtaining 0.73 g of the title compound. ESI(+) m/z: 721.3 [M+Na]$^+$.

$^1$H-NMR (DMSO-d6, 400M, BRUKER AV-400): δ (ppm) 7.33 (1H, d, =CH), 6.19 (1H, d), 5.82 (1H, s, =CH), 5.28 (1H, s), 5.15 (1H, d), 4.89-4.86 (1H, m), 4.83-4.78 (3H, m), 4.67-4.62 (1H, m,), 4.59 (1H, s), 4.46 (1H, d), 4.36-4.33 (1H, m), 4.27-4.22 (2H, m), 4.14-4.10 (2H, m), 3.81 (1H, m), 3.77 (1H, m), 3.61-3.59 (2H, m), 3.56-3.46 (3H, m), 3.43 (1H, m), 3.39-3.36 (2H, m), 3.29-3.25 (2H, m), 2.66-2.65 (1H, m), 2.57-2.53 (1H, m), 2.11-2.02 (2H, m), 1.62-1.59 (3H, m), 1.42 (1H, m), 1.38 (3H, s, —CH$_3$), 1.31-1.29 (1H, m), 1.05-1.04 (3H, d, —CH$_3$), 0.87-0.84 (1H,m), 0.77 (3H, s, —CH$_3$), 0.72-0.66 (1H, m).

Preparation Example 4

(11β,16α)-9-fluoro-11,17-dihydroxyl-16-methyl-21-{[4-O-(β-D-galactopyranosyl)-D-fructofuranosyl]oxy}pregna-1,4-diene-3,20-dione (Compound 4)

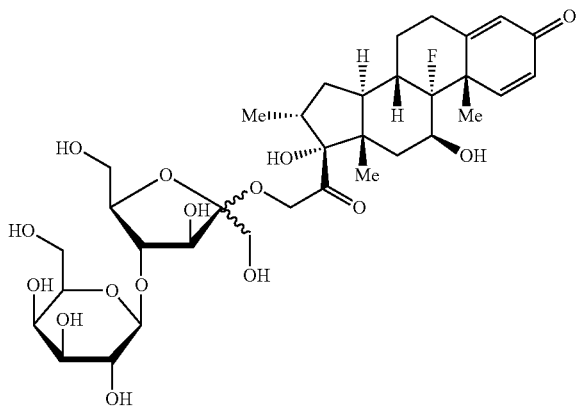

The Preparation Example 4 is implemented in a way similar to the Preparation Example 1 except that prednisolone is replaced by dexamethasone, obtaining 0.95 g of the title compound. ESI(+) m/z: 739.3 [M+Na]$^+$.

$^1$H-NMR (DMSO-d6, 400M, BRUKER AV-400): δ (ppm) 7.30 (1H, d, =CH), 6.24 (1H, d, =CH), 6.01 (1H, s, =CH), 5.32-5.27 (1H, m), 5.16 (1H, d), 5.08 (1H, s), 4.88-4.80 (4H, m), 4.72-4.64 (2H, m), 4.47 (1H, s), 4.36 (1H, m), 4.27-4.22 (1H, m), 4.15-4.13 (3H, m), 3.83-3.79 (2H, m), 3.60-3.53 (5H, m), 3.44 (2H, m), 3.29 (2H, m), 2.92 (1H, m), 2.67-2.59 (1H, m), 2.39-2.31 (2H, m), 2.16-2.06 (2H, m), 1.76 (1H, m), 1.66-1.58 (1H, m), 1.52 (1H, m), 1.49 (3H, s, —CH$_3$), 1.36-1.34 (1H, m), 1.06 (1H, m), 0.87 (3H, s, —CH$_3$), 0.79 (3H, d, —CH$_3$).

Preparation Example 5

(11β,16β)-9-fluoro-11,17-dihydroxyl-16-methyl-21-{[4-O-(β-D-galactopyranosyl)-D-fructofuranosyl]oxy}pregna-1,4-diene-3,20-dione (Compound 5)

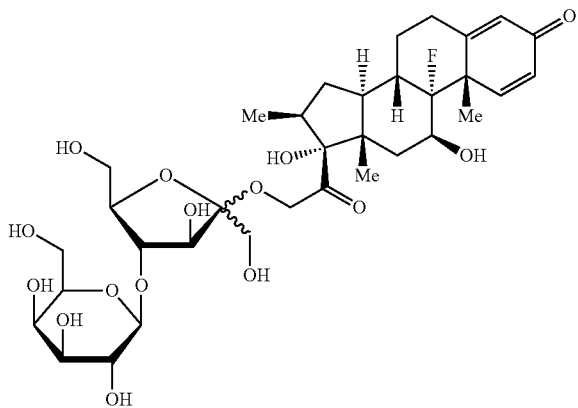

The Preparation Example 5 is implemented in a way similar to the Preparation Example 1 except that prednisolone is replaced by betamethasone, obtaining 0.58 g of the title compound. ESI(+) m/z: 739.3 [M+Na]$^+$.

$^1$H-NMR (DMSO-d6, 400M, BRUKER AV-400): δ (ppm) 7.30 (1H, d, =CH), 6.23 (1H, d, =CH), 6.01 (1H, s, =CH), 5.24 (1H, s), 5.20 (1H, d), 5.14-5.12 (1H, d), 4.88-4.77 (4H, m), 4.60-4.55 (1H, m), 4.47 (1H, d), 4.40-4.35 (1H, m), 4.29-4.24 (1H, m), 4.14-4.10 (3H, m), 3.85-3.83 (1H, m), 3.79-3.77 (1H, m), 3.60-3.46 (5H, m), 3.45-3.42 (1H, m), 3.40-3.36 (2H, m), 3.30 (2H, m), 2.66-2.60 (1H, m), 2.46-2.32 (2H, m), 2.09-2.07 (2H, m), 1.98-1.82 (3H, m), 1.49 (3H, s, —CH$_3$), 1.40-1.34 (2H, m), 1.04-1.02 (2H, m), 0.95 (3H, s, —CH$_3$).

Preparation Example 6

(11β,16α)-9-fluoro-11,16,17-trihydroxyl-21-{[4-O-(β-D-galactopyranosyl)-D-fructofuranosyl]oxy}pregna-1,4-diene-3,20-dione (Compound 6)

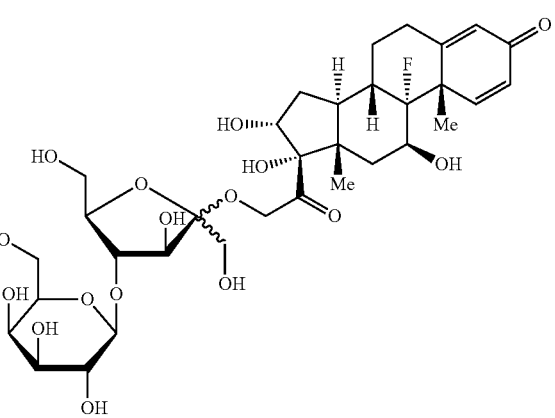

The Preparation Example 6 is implemented in a way similar to the Preparation Example 1 except that prednisolone is replaced by triamcinolone, obtaining 0.38 g of the title compound. ESI(+) m/z: 741.3 [M+Na]$^+$.

Preparation Example 7

(11β,16α)-11-hydroxyl-16,17-(butylidenedioxy)-21-{[4-O-(β-D-galactopyranosyl)-D-fructofuranosyl]oxy}pregna-1,4-diene-3,20-dione (Compound 7)

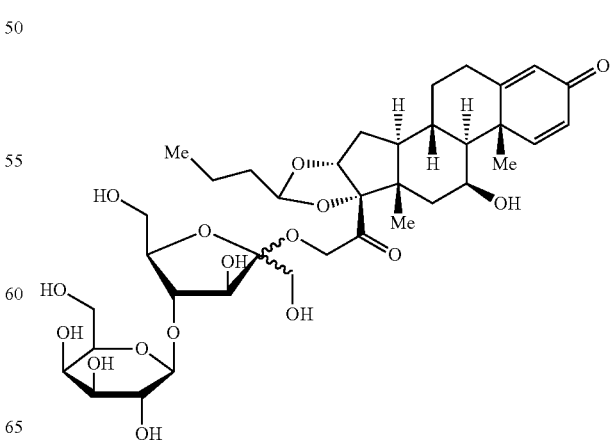

The Preparation Example 7 is implemented in a way similar to the Preparation Example 1 except that prednisolone is replaced by budesonide, obtaining 1.2 g of the title compound. ESI(+) m/z: 777.3 [M+Na]$^+$.

$^1$H-NMR (DMSO-d6, 400M, BRUKER AV-400): δ (ppm) 7.32 (1H, d, =CH), 6.18 (1H, d, =CH), 5.92 (1H, s, =CH), 5.19-5.17 (1H, m), 5.14 (1H, m), 5.05 (1H, d), 4.81-4.75 (4H, m), 4.71 (1H, m), 4.64-4.62 (1H, d), 4.59-4.57 (1H, m), 4.45 (1H, m), 4.35 (2H, m), 4.31-4.24 (2H, m), 4.15-4.13 (2H, m), 3.82-3.75 (2H, m), 3.60 (3H, m), 3.57-3.53 (3H, m), 3.45-3.43 (3H, m), 3.40-3.37 (2H, m), 3.29 (2H, m), 2.77-2.67 (1H, m), 2.31 (1H, m), 2.09 (1H, s), 1.98 (2H, m), 1.79-1.72 (3H, m), 1.61-1.52 (4H, m), 1.42 (2H, m), 1.38 (3H, s, —CH$_3$), 1.35-1.23 (2H, m), 1.15-1.11 (1H, m), 1.07-1.04 (3H, t, —CH$_3$), 1.01-0.93 (2H, m), 0.88 (1H, m), 0.86 (3H, s, —CH$_3$), 0.81 (1H, s).

Preparation Example 8

2-methyl-5-nitro-1-{2-{[4-O-(β-D-galactopyranosyl)-D-fructofuranosyl]oxy}ethyl}imidazole (Compound 8)

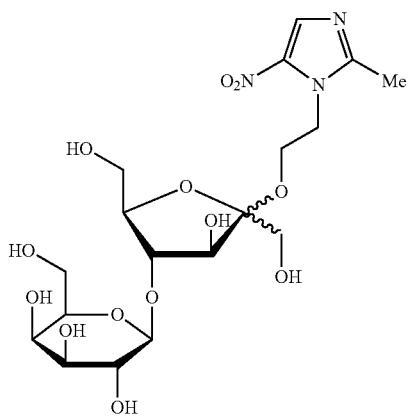

The Preparation Example 8 is implemented in a way similar to the Preparation Example 1 except that prednisolone is replaced by metronidazole, obtaining 1.9 g of the title compound. ESI(+) m/z: 518.2 [M+Na]$^+$.

$^1$H-NMR (DMSO-d6, 400M, BRUKER AV-400): δ (ppm) 8.03 (1H, s, Ar—H), 5.06-5.04 (1H, d), 4.87-4.85 (1H, d), 4.82-4.79 (1H, d), 4.76 (2H, m), 4.47-4.43 (3H, m), 4.35-4.32 (1H, t), 4.09-4.07 (1H, d), 3.94-3.91 (1H, t), 3.81-3.79 (2H, t), 3.72-3.69 (1H, m), 3.60 (1H, m), 3.54-3.49 (2H, m), 3.48-3.39 (5H, m), 3.34-3.27 (3H, m), 2.48 (3H, s, —CH$_3$).

Preparation Example 9

6-[(1-methyl-4-nitro-1H-imidazol-5-yl)thio]-9-[4-O-(β-D-galactopyranosyl)-D-fructofuranosyl]-9H-purine (Compound 9)

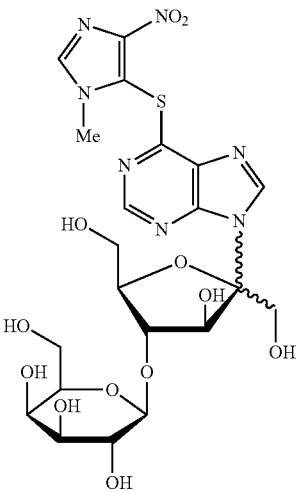

Step I:

At room temperature, 10.0 g lactulose (0.029 mol) was added into a reaction flask, and then 45.0 g acetic anhydride (0.435 mol) and 34.4 g pyridine (0.43 mol) were sequentially added thereto. The mixture was stirred for about 1 h to become clear, stirred for 14 hours at room temperature, and concentrated under reduced pressure to evaporate acetic acid, pyridine and acetic anhydride. The residue was purified with column chromatography using petroleum ether/ethyl acetate to obtain 16.5 g of a product, octa-acetyl lactulose (Compound F), at a yield of 83.2%.

Step II:

Under an argon atmosphere, azathioprine (1.5 g, 5.4 mmol), N,O-bis(trimethylsilyl)acetamide (BSA) (1.3 g, 6.48 mmol), acetonitrile (50 ml) were mixed and stirred, heated to reflux for 3 hours, and then cooled to 0° C. To the mixture, the above Compound F (5.5 g, 8.1 mmol) was added, and then TMSOTf (2.2 g, 10 mmol) was added dropwise. After that, the temperature was increased to room temperature, and the reaction was performed for 4 hours.

130 ml of a saturated sodium bicarbonate solution and 100 ml of dichloromethane were added to the reaction solution. The solution was separated. The aqueous phase was extracted with dichloromethane (50 ml, twice). The extraction organic phases were combined, dried, and purified with column chromatography to obtain 2.24 g of a compound at a yield of 46.3%. ESI(+) m/z: 918.3 [M+Na]$^+$.

Step III: Preparation of Compound 9:

The above product of Step II (2.0 g, 2.2 mmol) was dissolved in 20 ml methanol. 10 ml lithium hydroxide solution (1M) was added thereto. The mixture was stirred at room temperature overnight.

The reaction solution was neutralized to be neutral and concentrated to dryness under reduced pressure. 30 ml water and 10 ml methyl tert-butyl ether were added to the residue. After the residue was dissolved, the solution was separated. The aqueous phase product was separated by C18 reversed phase preparative chromatography to obtain 0.51 g of a solid, i.e., the title compound (Compound 9), at a yield of 38.0%. ESI(+) m/z: 602.2 [M+H]+.

¹H-NMR (DMSO-d6, 400M, BRUKER AV-400): δ (ppm) 8.60-8.55 (2H, Ar—H), 8.25 (1H, s, Ar—H), 5.05 (1H, d), 4.86 (1H, d), 4.83-4.76 (3H, m), 4.50-4.32 (2H, m), 4.08 (1H, d), 3.92 (1H, t), 3.71-3.69 (4H, m), 3.60-3.50 (3H, m), 3.50-3.25 (8H, m).

Preparation Example 10

6-thio-9-[4-O-(β-D-galactopyranosyl)-D-fructofuranosyl]-9H-purine (Compound 10)

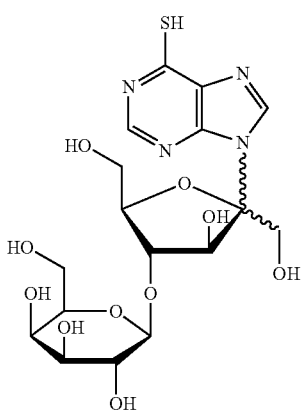

The Preparation Example 10 is implemented in a way similar to the Preparation Example 9 except that azathioprine is replaced by 6-mercaptopurine, obtaining 1.1 g of the title compound. ESI(+) m/z: 477.2 [M+H]+.

¹H-NMR (DMSO-d6, 400M, BRUKER AV-400): δ (ppm) 8.38 (1H, s, Ar—H), 8.18 (1H, s, Ar—H), 5.04 (1H, d), 4.85 (1H, d), 4.85-4.75 (3H, m), 4.50-4.30 (2H, m), 4.08 (1H, d), 3.90 (1H, t), 3.72 (1H, m), 3.60-3.50 (3H, m), 3.50-3.25 (8H, m).

Preparation Example 11

5-fluoro-1-[4-O-(β-D-galactopyranosyl)-D-fructofuranosyl]pyrimidine-2,4(1H,3H)-dione (Compound 11)

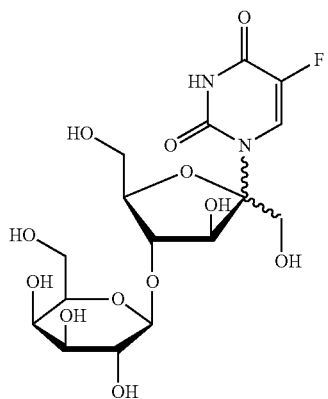

The Preparation Example 11 is implemented in a way similar to the Preparation Example 9 except that azathioprine is replaced by 5-fluorouracil, obtaining 0.65 g of the title compound. ESI(−) m/z: 453.1

Preparation Example 12

N-{2-[(S)-1-(3-ethoxy-4-methoxyphenyl)-2-(methylsulfonyl)ethyl]-1,3-dioxo-2,3-dihydro-1H-isoindol-4-yl}-N'-[4-O-(β-D-galactopyranosyl)-D-fructofuranosyl]acetamide (Compound 12)

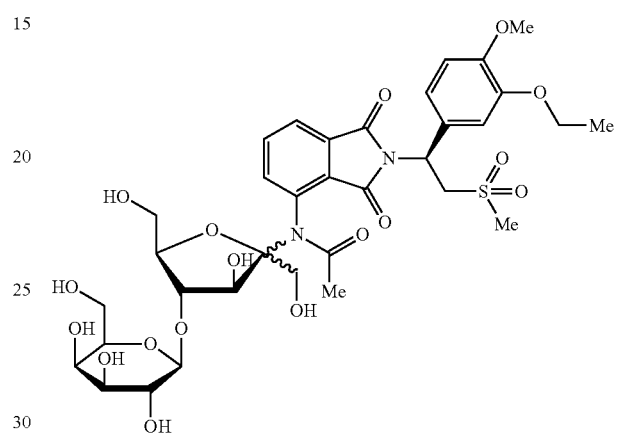

The Preparation Example 12 is implemented in a way similar to the Preparation Example 9.

Step I is the same as Step I of the Preparation Example 9.

Step II:

0.67 g apremilast (1.45 mmol), BSA (2.18 mmol) and 3 ml acetonitrile were added into a reaction flask at room temperature. The mixture was heated to reflux for 3 hours and then cooled to room temperature. 1.0 g octa-acetyl lactulose (Compound F, the product of Step I in Preparation Example 9) (1.45 mmol) was added thereto. After that, the mixture was stirred for 5 minutes to become clear. 0.55 g TMSOTf (2.47 mmol) was slowly added dropwise thereto. After that, the solution was stirred for 14 hours at room temperature.

At 0° C., 10 ml of a saturated sodium bicarbonate solution and 20 ml dichloromethane were added to the reaction solution. The solution was separated. The aqueous phase was extracted with dichloromethane (10 ml, twice). The extraction organic phases were combined, dried, and then concentrated to dryness under reduced pressure. The residue was purified with column chromatography using dichloromethane/methanol system to obtain 263 mg of a solid product, i.e., apremilast hepta-acetyl lactuloside, at a yield of 16.7%. ESI(+) m/z: 1101.4 [M+Na]+.

Step III: Preparation of Compound 12

100 mg of the above product of Step II was dissolved in 5 ml methanol. Then, 5 ml of a magnesium methoxide solution in methanol (7-8%) was added thereto. The solution was stirred at room temperature for 5 hours. The reaction solution was neutralized with a saturated ammonium chloride solution, and concentrated to dryness. The residue was dissolved in 5 ml water. The insoluble matter was filtered off. The filtrate was purified with C18 reverse phase preparative chromatography (using methanol-water as eluent). The eluate was concentrated to dryness under reduce pressure to obtain 45 mg of the title compound (Compound 12) at a yield of 61.8%. ESI(+) m/z: 807.3 [M+Na]⁺.

¹H-NMR (DMSO-d6, 400M, BRUKER AV-400): δ (ppm) 8.0-7.8 (3H, m Ar—H), 7.2-6.9 (3H, m, Ar—H), 5.79 (1H, m), 5.0-4.53 (5H, m), 4.50-4.20 (4H,m), 4.20-3.83 (6H,m), 3.74 (3H, s), 3.67-3.10 (10H, m), 3.0 (3H, m), 2.51 (3H, s), 1.32 (3H, t).

Preparation Example 13

17-hydroxyl-21-{[4-O-(β-D-galactopyranosyl)-D-fructofuranosyl]oxy}pregna-1,4-diene-3,11,20-trione (Compound 17)

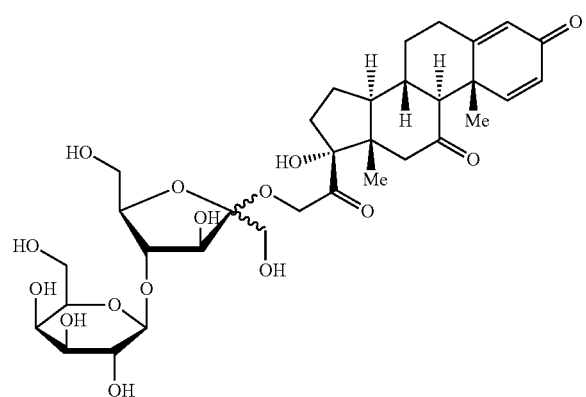

The Preparation Example 13 is implemented in a way similar to the Preparation Example 1 except that prednisolone is replaced by prednisone, obtaining 1.5 g of the title compound. ESI(+) m/z: 705.3 [M+Na]⁺.

Preparation Example 14

4-amino-5-chloro-2,3-dihydro-N-[1-(3-methoxypropyl)-4-piperidinyl]-N'-[4-O-(β-D-galactopyranosyl)-D-fructofuranosyl]-7-benzofurancarboxamide (Compound 13)

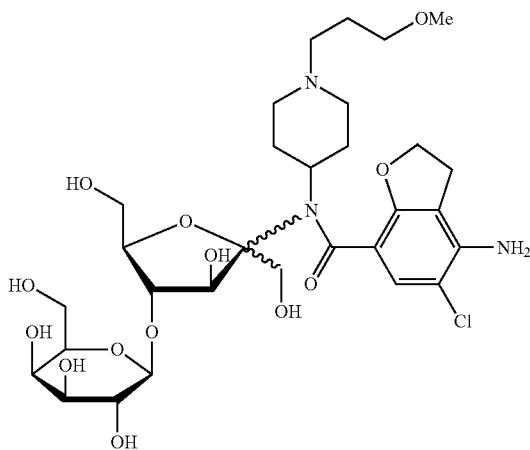

Step I: Preparation of Compound K 2.0 g octa-benzoyl lactulose (Compound A in Preparation Example 1) was dissolved in 2.5 M of a hydrogen chloride solution (10 ml) in glacial acetic acid. The reaction solution was stirred for 4 hours at room temperature. When it is monitored by TLC that the raw materials disappeared, the reaction solution was concentrated under reduced pressure at 50° C. to evaporate the solvent. The residue was pulpified with diethyl ether and filtered to obtain 1.8 g of a Compound (K) crude product, which was directly used in next reaction.

Step II: Preparation of Compound M 1.8 g Compound K crude product, 0.54 g (1.47 mmol) prucalopride and 10 ml toluene were mixed and stirred at room temperature. 3 droplets of triethylamine were added dropwise thereto. The reaction solution was stirred at 70° C. for 8 hours. Then, the reaction solution was concentrated to dryness under reduced pressure. The residue was purified with silica gel column chromatography (dichloromethane/methanol) to obtain 0.7 g of a product (Compound M) at a yield of 33.6%. ESI(+) m/z: 1442.5 [M+Na]⁺.

Step III: Preparation of Compound 13

0.68 g Compound M (0.48 mmol) was dissolved in 10 ml tetrahydrofuran at room temperature. 20 mg (0.37 mmol) sodium methoxide was added thereto. The reaction solution was stirred at room temperature for 4 hours. After the completion of the reaction, the reaction solution was concentrated under reduced pressure to evaporate to dryness at 45° C. The residue was dissolved in 5 ml water, and washed with dichloromethane (5 ml, 3 times). The pH of the aqueous phase was adjusted to 8 with dilute acetic acid. Then, the aqueous phase was washed with dichloromethane (5 ml, twice). The aqueous solution of the obtained product was purified with C18 reverse phase preparative chromatography (using methanol-water as an eluent). The collected fraction was concentrated under reduced pressure to evaporate to dryness at 50° C. to obtain 0.18 g of a white solid, i.e., the title compound (Compound 13), at a yield of 54.2%.

ESI(+) m/z: 692.3 [M+H]⁺.

Chemical purity: 95.0% (HPLC method)

HPLC method:

Chromatographic column: octadecyl silane bonded silica gel column; column temperature: 35° C.; detection wavelength: 240 nm Mobile phase:

A MeOH:CH₃CN (2:1)

B 10 mmol/L potassium dihydrogen phosphate (the pH was adjusted to 7.1 with phosphoric acid)

Gradient program: 0→20 min (B:70%→45%); 20→25 min (B:45%→70%); 25→29 min (B:70%→70%)

Retention time: 24.1 min

Preparation Example 15

5-chloro-2,3-dihydro-4-{[4-O-(β-D-galactopyranosyl)-D-fructofuranosyl]amino}-N-[1-(3-methoxypropyl)-4-piperidinyl]-7-benzofurancarboxamide (Compound 14)

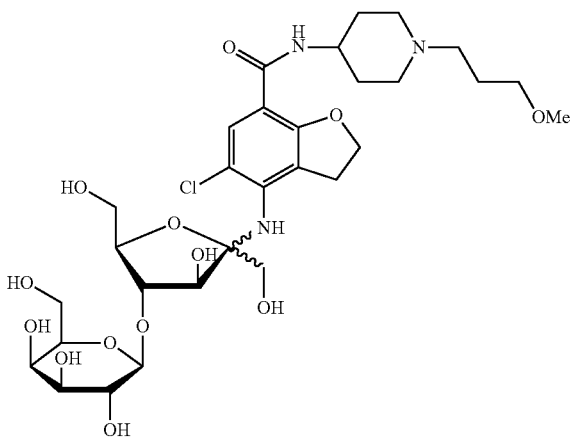

Step I: Preparation of Compound N 20.0 g octa-benzoyl lactulose (16.3 mmol, Compound A in Preparation Example 1), 5.0 g prucalopride (13.6 mmol), 40 g anhydrous sodium sulfate and 100 ml acetonitrile were sequentially added into a reaction flask at room temperature. Under the protection of argon, tert-butyldimethylsilyl trifluoromethanesulfonate (TBSOTf, 7.1 g, 27.2 mmol) was added dropwise thereto. After that, the reaction was performed at room temperature for 3 hours. 4.1 g trimethyl pyridine was diluted with 10 ml dichloromethane, and then slowly added dropwise to the reaction system to quench the reaction. The reaction mixture was stirred for 30 minutes, filtered, and washed with dichloromethane. The filtrate was concentrated under reduced pressure to evaporate to dryness at 45° C. The residue was purified with silica gel column chromatography (dichloromethane/methanol) to obtain 7.5 g of a product (Compound N) at a yield of 38.8%. ESI(+) m/z: 1442.5 [M+Na]$^+$.

Step II: Preparation of Compound 14

The above product of Step I (Compound N, 1.8 g, 1.27 mmol) was dissolved in 15 ml tetrahydrofuran at room temperature. 30 mg (0.56 mmol) sodium methoxide was added thereto. The reaction solution was stirred at room temperature for 4 hours. After the completion of the reaction, the reaction solution was concentrated under reduced pressure to evaporate to dryness at 45° C. The residue was dissolved in 5 ml water, and washed with dichloromethane (5 ml, 3 times). The pH of the aqueous phase was adjusted to 8 with dilute acetic acid. Then, the aqueous phase was washed with dichloromethane (5 ml, twice). The aqueous solution of the obtained product was purified with C18 reverse phase preparative chromatography (using methanol-water as eluent). The collected fraction was concentrated under reduced pressure to evaporate to dryness at 50° C. to obtain 0.36 g of a white solid, i.e., the title compound (Compound 14), at a yield of 40.9%. Chemical purity: 96.0% (HPLC method)

ESI(+) m/z: 692.3 [M+H]$^+$.

$^1$H-NMR (DMSO-d6, 400M, BRUKER AV-400): δ (ppm) 7.57-7.45 (2H,m), 5.66 (1H,s), 5.41 (1H,s), 4.75-4.60 (4H, m), 4.34 (1H,m), 4.08 (1H,m), 4.0-3.82 (3H,m), 3.80-3.70 (2H,m), 3.70-3.62 (2H,m), 3.62-3.30 (12H,m), 3.24 (2H,m), 3.21 (3H,s), 2.70 (2H,m), 2.30 (2H,m), 2.04 (2H,m), 1.79 (2H,m), 1.64 (2H,m), 1.45 (2H,m).

The HPLC method is the same as that in Preparation Example 14. Retention time: 13.9 min.

Preparation Example 16

6-{N-methyl-N'-[(3R,4R)-4-methyl-1-(2-cyanoacetyl)piperidin-3-yl]amino}9-[4-O-(β-D-galactopyranosyl)-D-fructofuranosyl]-9H-purine (Compound 18)

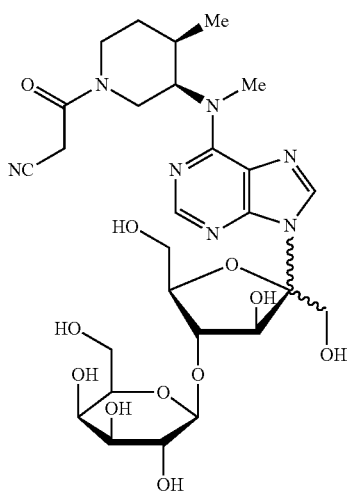

The Preparation Example 16 is implemented in a way similar to the Preparation Example 9 except that azathioprine is replaced by tofacitinib, obtaining 0.25 g of the title compound. ESI(+) m/z: 638.5 [M+H]$^+$.

Various formulations (such as tablets, enteric granules, and capsules) were prepared by using the compound represented by Formula (I) according to the present disclosure below, and the formulations and specific preparation methods thereof are shown in the following examples.

Formulation Example 1

Tablets were prepared by using Compound 1 prepared according to the present disclosure as an active pharmaceutical ingredient in accordance with the formulations as shown in Table 2 below.

TABLE 2

| 1000 tablets | Tablet formulation 1 | Tablet formulation 2 | Tablet formulation 3 | Tablet formulation 4 |
|---|---|---|---|---|
| Tablet core | Compound 1 5 g<br>Lactose 70 g<br>Microcrystalline cellulose 29 g<br>Magnesium stearate 1 g | Compound 1 5 g<br>Lactose 60 g<br>Microcrystalline cellulose 17 g<br>Magnesium stearate 1 g<br>Calcium carbonate 20 g<br>Hydroxypropyl cellulose 20 g | Compound 1 5 g<br>Lactose 70 g<br>Microcrystalline cellulose 29 g<br>Magnesium stearate 1 g | Compound 1 5 g<br>Lactose 70 g<br>Microcrystalline cellulose 29 g<br>Magnesium stearate 1 g |

TABLE 2-continued

| 1000 tablets | Tablet formulation 1 | Tablet formulation 2 | Tablet formulation 3 | Tablet formulation 4 |
|---|---|---|---|---|
| Coating film | | | Opadry 5 g | Eudragit L30D-55 20 g Talc powder 1.8 g Triethyl citrate 0.5 g |

Here, in the preparation of tablet formulations 1, 3 and 4, all components of the tablet cores were mixed and then pressed into tablets.

In the preparation of tablet formulation 2, in addition to magnesium stearate and microcrystalline cellulose, an aqueous solution of hydroxypropyl cellulose (5%) was added. The mixture was wet granulated and dried. Finally, magnesium stearate was added thereto. The mixture was totally blended and pressed into a tablet.

In the preparation of table formulation 3, an aqueous dispersion of Opadry (gastrically dissolved film coating powder, Shanghai Colorcon Company) was used as the coating. Any conventional efficient coating pan may be used.

In the preparation of tablet formulation 4, for the preparation of the coating, 20 g Eudragit L30D-55 (Evonik_Rhom, Rohm Resin Company, Germany), 1.8 g talc powder and 0.5 g triethyl citrate were diluted with appropriate amount of water, stirred uniformly, and made into the coating in an efficient coating pan according to conventional coating process parameters.

Formulation Example 2

Enteric granules were prepared by using Compound 1 prepared according to the present disclosure as an active pharmaceutical ingredient in accordance with the formulations as shown in Table 3 below.

TABLE 3

| Formulation of Enteric granule | |
|---|---|
| Microcrystalline cellulose granule core (particle diameter: 0.2 to 0.4 mm) | 200 g |
| Compound 1 | 3.0 g |
| Hydroxypropyl cellulose E5 | 6 g |
| Talc powder | 4 g |
| Water | 200 ml |
| Drug loading | |
| Eudragit L30D-55 | 100 g |
| Triethyl citrate | 4.5 g |
| Talc powder | 15 g |
| Water | 180 ml |
| Enteric coating layer | |

The Compound 1, hydroxypropyl cellulose, and talc powder in the drug loading formulation were dissolved and dispersed in water to obtain a drug loading solution. The granule cores were fluidized in a fluid bed (WBF-1G, Chongqing Enger Granulating & Coating Technology Co., Ltd.). With set parameters (inlet air: 50 m³/h, temperature: 40-50° C., atomizing pressure: 1.0 bar), the drug loading solution was bottom sprayed at a flow rate of 2-3 g/min, and the material temperature was controlled at 30±3° C. After the completion of the drug loading, the enteric coating layer was coated.

The materials in the enteric coating layer formulation were mixed homogeneously, and coated according to the above process parameters to obtain enteric granules.

Formulation Example 3

Capsules were prepared by using Compound 7 prepared according to the present disclosure as an active pharmaceutical ingredient in accordance with the formulations as shown in Table 4 below.

TABLE 4

| | Capsule formulation 1 | Capsule formulation 2 | Capsule formulation 3 |
|---|---|---|---|
| Content | Compound 7 1 g Starch 70 g lactose 29 g Fine powder silica gel 2 g Magnesium stearate 1 g | Compound 7 1 g Microcrystalline cellulose 60 g lactose 39 g Fine powder silica gel 5 g | Compound 7 1 g Microcrystalline cellulose 60 g lactose 18 g Lactulose 10 g Fine powder silica gel 5 g Pre-gelled starch 10 g |
| Capsule shell | Gelatin empty capsule (Huangshan Capsule Co., Ltd., Anhui) | Enteric gelatin empty capsule (Qiangji Pharmaceutical Co., Ltd., Chaozhou) | Colonically dissolved gelatin empty capsule (Qiangji Pharmaceutical Co., Ltd., Chaozhou) |

In the preparation of the medicament, the above contents were mixed homogeneously, and filled into the capsule shell to obtain a capsule.

Formulation Example 4

Tablets were prepared by using Compound 12 prepared according to the present disclosure as an active pharmaceutical ingredient in accordance with the formulations as shown in Table 5 below.

TABLE 5

| | Tablet formulation 1 | Tablet formulation 2 | Tablet formulation 3 |
|---|---|---|---|
| Tablet core | Compound 12 50 g Lactose 100 g Microcrystalline cellulose 100 g Calcium carbonate 100 g | Compound 12 50 g Lactose 100 g Microcrystalline cellulose 100 g | Compound 12 50 g Lactose 200 g Microcrystalline cellulose 10 g |
| Disintegrant | | Crosslinked sodium carboxymethyl cellulose 50 g | Crosslinked povidone 50 g |
| Binder | Hydroxypropyl cellulose 50 g | Hydroxypropyl cellulose 50 g | Sodium carboxymethyl cellulose 30 g |
| Lubricant | Magnesium stearate 5 g | Magnesium stearate 10 g | Magnesium stearate 10 g |
| Coating film | | Opadry 30 g | Eudragit L30D-55 100 g Talc powder 9 g Triethyl citrate 2.5 g |

During the preparation of the medicament, all tablets were prepared with wet granulation. Here, the components of the tablet core were firstly mixed, and then an aqueous solution of the binder was added thereto. The mixture was wet granulated and then dried. After that, a disintegrant and a lubricant were added thereto. The mixture was totally blended and pressed into a tablet.

Coating was performed with conventional coating process.

Test on the Properties of the Compounds

In the present application, the compound represented by formula (I) according to the present disclosure were tested for the in vitro stability, systemic pharmacokinetics in animal body, localized pharmacokinetic characteristic in gastrointestinal tract, and the like.

Test on Stability in Mediums In Vitro

At 37° C., Compound 17 was incubated in different mediums (buffer solutions with different pH, a simulated intestinal fluid containing pancreatin, and simulated gastric fluid containing pepsin). As shown in table 6 below, sampling was performed at interval times, and the percentages of Compound 17 and its degradation product (i.e., the original form of prednisone) were determined by HPLC method, where the amount of each ingredient was calculated by normalization. In the analysis results, the higher the percentage of Compound 17, the lower the percentage of the degradation product was, indicating that Compound 17 was more stable. The results in table 6 indicate that when the pH was 2.0 or higher, within 1.5 hours, the percentage of remaining Compound 17 was greater than 80%, and the percentage of the degradation product was less than 20%, suggesting a higher resistance to gastric acid.

Stability in the Presence of Colon Flora

A phosphate buffer solution with a pH of 7.0 was formulated, and then $CO_2$ was introduced to the solution to adjust the pH to 6.8. Then, the content in colon of a male SD rat (body weight: 180-220 g) was placed in a water bath at 37° C., and added into the phosphate buffer solution with a pH of 6.8 as prepared above under the protection of $N_2$ to a concentration of 20% (w/v). The buffer solution was kept in an oxygen-free environment. Then, the test Compound 17 was added to the buffer solution, and the solution was stirred uniformly.

As shown in table 7 below, 0.5 ml sample solutions were collected at regular intervals, and 1.0 ml acetone precipitated protein was added thereto; and the mixture was mixed homogeneously, left standing for 2 minutes, and then centrifuged (12000 rpm, 5 min). Supernatant was analyzed with HPLC, where the amount of each ingredient was calculated by normalization. As shown in table 7, Compound 17 was prone to degradation in a phosphate buffer solution with a pH of 6.8, and about 90% of the compound was degraded in 3 hours with only 11.3% remained. The above results indicate that in the colon flora environment, Compound 17 can be rapidly degraded to remove the glycosidic bond, so as to produce an active drug and exert its efficacy timely.

TABLE 6

| Medium | | Time (h) | | | | |
| --- | --- | --- | --- | --- | --- | --- |
| | | 0 | 1 | 6 | 8 | 33 |
| Water (pH 6.2) | Compound 17 (%) | 97.6 | 97.6 | 97.6 | 98.2 | 98.0 |
| | Prednisone (%) | 0.0 | 0.0 | 0.0 | 0.0 | 0.0 |
| Phosphate buffer solution, pH 7.8 | Compound 17 (%) | 97.5 | 97.6 | 97.6 | 97.6 | 97.7 |
| | Prednisone (%) | 0.0 | 0.0 | 0.0 | 0.0 | 0.0 |
| Phosphate buffer solution, pH 6.8 | Compound 17 (%) | 97.3 | 97.5 | 99.0 | 99.0 | 97.6 |
| | Prednisone (%) | 0.0 | 0.0 | 0.0 | 0.0 | 0.0 |
| Phosphate buffer solution, pH 5.8 | Compound 17 (%) | 99.5 | 97.3 | 99.4 | 99.5 | 99.3 |
| | Prednisone (%) | 0.0 | 0.0 | 0.0 | 0.0 | 0.1 |
| Simulated intestinal fluid (containing pancreatin) (pH 6.8) | Compound 17 (%) | 97.6 | 97.4 | 97.7 | 97.7 | 96.2 |
| | Prednisone (%) | 0.0 | 0.0 | 0.0 | 0.0 | 0.8 |

| Medium | | Time (h) | | | | | | | | | |
| --- | --- | --- | --- | --- | --- | --- | --- | --- | --- | --- | --- |
| | | 0 | 0.5 | 1 | 1.5 | 2 | 3 | 4 | 8 | 20 | 24 |
| Hydrochloric acid solution, pH 2.0 | Compound 17 (%) | 99.7 | 93.3 | 86.5 | 80.1 | 74.6 | 64.5 | 55.3 | 30.8 | — | 2.5 |
| | Prednisone (%) | 0.3 | 6.3 | 13.2 | 19.7 | 25.0 | 35.1 | 44.2 | 68.5 | — | 94.8 |
| Acetate buffer solution, pH 4.0 | Compound 17 (%) | 99.6 | 99.6 | 99.5 | 99.4 | — | — | 99.2 | — | 97.1 | 96.5 |
| | Prednisone (%) | 0.0 | 0.0 | 0.1 | 0.3 | — | — | 0.4 | — | 2.2 | 2.7 |
| Hydrochloric acid solution, pH 1.2 | Compound 17 (%) | 96.0 | 47.1 | 22.1 | — | 4.5 | 1.0 | — | — | — | — |
| | Prednisone (%) | 4.0 | 52.4 | 76.6 | — | 92.4 | 96.1 | — | — | — | — |
| Simulated gastric fluid (containing pepsin) (pH 2.0) | Compound 17 (%) | 97.0 | 53.6 | 28.9 | 15.6 | 7.0 | 2.1 | — | — | — | — |
| | Prednisone (%) | 3.0 | 45.8 | 70.3 | 83.3 | 89.8 | 95.2 | — | — | — | — |

TABLE 7

| | Time (h) | | | | |
|---|---|---|---|---|---|
| | 0 | 1 | 2 | 3 | 20 |
| Compound 17 (%) | 84.8 | 49.0 | 25.3 | 11.3 | 0.0 |
| T14.148 (%) | 13.5 | 42.5 | 59.1 | 65.5 | 12.7 |
| T14.713 (%) | 0.0 | 0.0 | 0.0 | 0.0 | 19.2 |
| Prednisone (%) | 1.7 | 8.1 | 14.7 | 21.2 | 39.7 |
| T16.392 (%) | 0.0 | 0.0 | 0.0 | 0.0 | 6.4 |
| T22.624 (%) | 0.0 | 0.0 | 0.0 | 0.0 | 7.8 |

Note: in the above table, "T14.148 (%)" represents the percentage of peak area of the material with a retention time of 14.148 min "T14.713 (%)" represents the percentage of peak area of the material with a retention time of 14.713 min. "T16.392 (%)" represents the percentage of peak area of the material with a retention time of 16.392 min. "T22.624 (%)" represents the percentage of peak area of the material with a retention time of 22.624 min.

Other typical example compounds were tested for stability according to the above method, and the test results are shown in Table 8 below.

TABLE 8

Stability of some example compounds in mediun

| | Medium (time) | | |
|---|---|---|---|
| Composition | Water (pH 1.2) (2 h) | Simulated intestinal fluid (containing pancreatin) (pH 6.8) (8 h) | Content in colon (pH 6.8) (1 h) |
| Compound 1 (%) | 30.4 | 99.0 | 22.1 |
| Prednisolone (%) | 67.2 | 0.2 | 39.7 |
| Compound 4 (%) | 25.0 | 99.4 | 15.6 |
| Dexamethasone (%) | 72.7 | 0 | 50.3 |
| Compound 7 (%) | 20.0 | 98.9 | 27.2 |
| Budesonide (%) | 61.6 | 0.1 | 45.9 |
| Compound 12 | 20.0 | 100 | 30.1 |
| Apremilast | 79.8 | 0 | 45.6 |
| Compound 13 | 4.4 | 99.4 | 18.7 |
| Prucalopride | 95.0 | 0 | 65.4 |
| Compound 14 | nd | 98.3 | 2.1 |
| Prucalopride | 99.5 | 1.1 | 48.5 (prucalopride) 49.3 (intermediate state) |

Test on Systemic Pharmacokinetics and Localized Pharmacokinetic Characteristic in Gastrointestinal Tract of Compound 1 After Oral Administration to SD Rats Comparison research among systemic pharmacokinetics and localized pharmacokinetic characteristic in gastrointestinal tract of Compound 1 (Preparation Example 1), enteric granules comprising Compound 1 (Formulation Example 2) and the active ingredient thereof (prednisolone) after intragastric administration to SD rats was carried out to further evaluate the absorption and conversion procedures of Compound 1 in rat bodies and the main sites of conversion and release of the active ingredient, and to investigate whether the application of enteric formulation technology can overcome the disadvantage occurred in in vitro test that Compound 1 will be partially degraded in an acidic environment with a lower pH.

According to the experiments, 112 healthy SD male rats (body weight: 180-220 grams) were divided into 4 groups (prednisolone group, Compound 1 group, Compound 1 enteric granule group, and blank control group), wherein there were 36 animals in each of the prednisolone group, Compound 1 group, and Compound 1 enteric granule group, and there were 4 animals in the blank control group. Detailed administration regimen is as shown in Table 9 below.

TABLE 9

Administration regimen for pharmacokinetic research on SD rats to which Compound 1 was orally administered

| Group | Sample | Method and frequency of administration | Dosage (mg/kg) | Animal number |
|---|---|---|---|---|
| 1 | Prednisolone suspension | Intragastric perfusion (single) | 5 | 36 |
| 2 | Compound 1 suspension | Intragastric perfusion (single) | 9.55 (equivalent to 5 mg/kg prednisolone in mole) | 36 |
| 3 | Compound 1 enteric granule suspension | Intragastric perfusion (single) | 9.55 (equivalent to 5 mg/kg prednisolone in mole) | 36 |
| 4 | Blank control | Intragastric perfusion (single) | NA | 4 |

For the experiment animals of Group 1, Group 2 and Group 3, at each time point of 30 min, 1 h, 2 h, 3 h, 4 h, 5 h, 6 h, 8 h, and 10 h after the administration, 4 animals were randomly selected and sacrificed. The blood samples were collected, and the contents in the stomach and various segments of the intestine tract (the first half segment of the small intestine, the last half segment of the small intestine, the first third segment of the colon (including cecum), and the last two thirds segment of the colon) were weighed. The concentrations of prednisolone and Compound 1 in the plasma and the contents were determined by LC-MS/MS method, and the amounts of prednisolone and Compound 1 in various segments of the gastrointestinal tract were calculated based on the weights of the contents. 4 animals of Group 4 were sacrificed at the time point of 10 h. The blood samples and the contents in various segments of the gastrointestinal tract were collected as blank control.

For the prednisolone group, at different time points after the administration, the distribution of prednisolone in the contents of various sites of the gastrointestinal tract is as shown in Table 10 below. As seen from the results of Table 10, after prednisolone was intragastrically administered to rats, local prednisolone in the gastrointestinal tract was mainly distributed in the stomach and the small intestine, wherein the concentration of prednisolone in the stomach is the highest, while the concentrations of prednisolone in the contents of the cecum and colon sites were very low.

TABLE 10

Concentration of prednisolone in the contents at different sites of the gastrointestinal tract after intragastric perfusion of prednisolone

| | Concentration of prednisolone in the content (nmol/g), Mean ± SD | | | | |
|---|---|---|---|---|---|
| Time point (h) | Stomach | The first half segment of Small intestine | The last half segment of Small intestine | The first third segment (including cecum) of Colon | The last two thirds segment of Colon |
| 0.5 | 370.53 ± 46.38 | 16.66 ± 2.89 | 16.27 ± 3.34 | 0.32 ± 0.04 | — |
| 1 | 234.63 ± 30.40 | 19.20 ± 3.44 | 22.05 ± 3.56 | 0.54 ± 0.06 | — |
| 2 | 143.18 ± 18.32 | 51.92 ± 8.01 | 19.81 ± 2.77 | 0.41 ± 0.05 | 0.05 ± 0.01 |
| 3 | 90.91 ± 14.66 | 21.16 ± 2.18 | 20.47 ± 3.08 | 0.70 ± 0.11 | 0.10 ± 0.02 |
| 4 | 23.24 ± 4.27 | 17.38 ± 3.04 | 13.27 ± 2.09 | 0.66 ± 0.08 | 0.14 ± 0.02 |
| 5 | 1.29 ± 0.25 | 7.34 ± 1.38 | 6.94 ± 1.35 | 0.21 ± 0.03 | 0.09 ± 0.01 |
| 6 | 0.45 ± 0.06 | 0.36 ± 0.05 | 0.32 ± 0.06 | 0.13 ± 0.02 | 0.04 ± 0.01 |
| 8 | — | — | 0.04 ± 0.01 | — | — |
| 10 | — | — | — | — | — |

Figure 2:
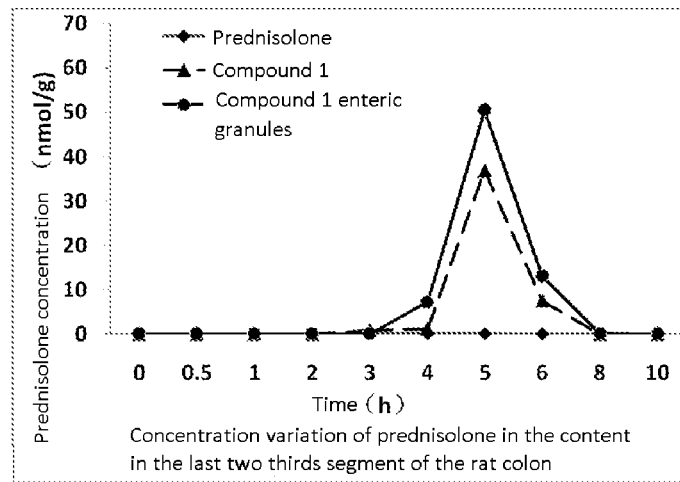
FIG. 2 shows the concentration variation of prednisolone in the content in the last two thirds of the colon of a rat after intragastric administration.

For the Compound 1 group and Compound 1 enteric granule group, the distributions of prednisolone in the contents of various sites of the rat gastrointestinal tract after the intragastric administration were respectively shown in Table 11 and Table 12 below. As compared to prednisolone group, the distributions in the gastrointestinal tract for the Compound 1 group and Compound 1 enteric granule group were significantly reduced, whereas the maximum concentrations ($C_{max}$) of local prednisolone in the cecum and colon sites were increased by a factor of 65-360 (see the results in Table 13), and the total exposure (AUC) was also much higher than the prednisolone (original form) group (see the drug-time curves in FIG. 1 and FIG. 2). Because the intragastric perfusion of enteric granules was used to prevent partial release of Compound 1 in the acidic environment at the stomach, no prednisolone would be substantially released at the stomach and the anterior segment of small intestine in the Compound 1 enteric granule group (all concentrations were below the limit of detection and could not be detected), and the concentration of local prednisolone in the colon was slightly higher than that in the Compound 1 group. The above results indicate that the release site of orally administered Compound 1 enteric granules is mainly at the cecum and the colon, and secondly at the posterior end of small intestine close to the cecum, which is in consistent with the object of the compound of the present disclosure.

TABLE 11

Concentration of prednisolone in the contents at different sites of the gastrointestinal tract after intragastric perfusion of Compound 1

| | Concentration of prednisolone in the content (nmol/g), Mean ± SD | | | | |
|---|---|---|---|---|---|
| Time point (h) | Stomach | The first half segment of Small intestine | The last half segment of Small intestine | The first third segment (including cecum) of Colon | The last two thirds segment of Colon |
| 0.5 | 10.85 ± 2.03 | 5.02 ± 0.75 | 1.31 ± 0.03 | — | — |
| 1 | 13.22 ± 1.87 | 2.14 ± 0.41 | 3.81 ± 0.62 | — | — |
| 2 | 55.37 ± 7.39 | 3.73 ± 0.39 | 15.17 ± 2.28 | — | — |
| 3 | 8.10 ± 1.21 | 0.36 ± 0.05 | 21.08 ± 3.64 | 9.43 ± 1.87 | 0.93 ± 0.17 |
| 4 | 9.74 ± 0.99 | 0.56 ± 0.07 | 39.50 ± 5.80 | 46.15 ± 6.74 | 1.21 ± 0.16 |
| 5 | 0.15 ± 0.02 | 0.42 ± 0.05 | 1.74 ± 0.31 | 19.27 ± 3.16 | 36.83 ± 6.24 |
| 6 | — | 0.29 ± 0.04 | 0.12 ± 0.02 | 5.91 ± 0.97 | 7.54 ± 1.01 |
| 8 | — | — | — | — | 0.03 ± 0.01 |
| 10 | — | — | — | — | — |

TABLE 12

Concentration of prednisolone in the contents at different sites of the gastrointestinal tract after intragastric perfusion of Compound 1 enteric granules

| | Concentration of prednisolone in the content (nmol/g), Mean ± SD | | | | |
|---|---|---|---|---|---|
| Time point (h) | Stomach | The first half segment of Small intestine | The last half segment of Small intestine | The first third segment (including cecum) of Colon | The last two thirds segment of Colon |
| 0.5 | — | — | — | — | — |
| 1 | — | — | — | — | — |

TABLE 12-continued

Concentration of prednisolone in the contents at different sites of the gastrointestinal tract after intragastric perfusion of Compound 1 enteric granules

| | Concentration of prednisolone in the content (nmol/g), Mean ± SD | | | | |
|---|---|---|---|---|---|
| Time point (h) | Stomach | The first half segment of Small intestine | The last half segment of Small intestine | The first third segment (including cecum) of Colon | The last two thirds segment of Colon |
| 2 | — | — | 1.33 ± 0.19 | — | — |
| 3 | — | — | 21.47 ± 3.37 | 11.05 ± 1.55 | — |
| 4 | — | — | 36.56 ± 4.02 | 61.34 ± 8.29 | 7.31 ± 0.98 |
| 5 | — | — | 2.60 ± 0.35 | 33.58 ± 5.31 | 50.46 ± 7.07 |
| 6 | — | — | 0.14 ± 0.02 | 10.47 ± 1.64 | 13.03 ± 2.36 |
| 8 | — | — | — | — | 0.08 ± 0.02 |
| 10 | — | — | — | — | — |

TABLE 13

Comparison among prednisolone concentration $C_{max}$ values in the contents of various sites of the gastrointestinal tract for different groups

| Group | Stomach | The first half segment of Small intestine | The last half segment of Small intestine | The first third segment (including cecum) of Colon | The last two thirds segment of Colon |
|---|---|---|---|---|---|
| | $C_{max}$ value of prednisolone in the content (nmol/g) | | | | |
| Prednisolone group | 370.53 | 51.92 | 22.05 | 0.70 | 0.14 |
| Compound 1 group | 55.37 | 5.02 | 39.50 | 46.15 | 36.83 |
| Compound 1 enteric granule group | 0.00 | 0.00 | 36.56 | 61.34 | 50.46 |
| | Ratio of $C_{max}$ of Compound 1 enteric granule group to $C_{max}$ of prednisolone group | | | | |
| Compound 1 group/ Prednisolone group | 0.15 | 0.10 | 1.79 | 65.93 | 263.07 |
| Compound 1 enteric granule group/prednisolone group | 0.00 | 0.00 | 1.66 | 87.63 | 360.43 |

Figure 3:
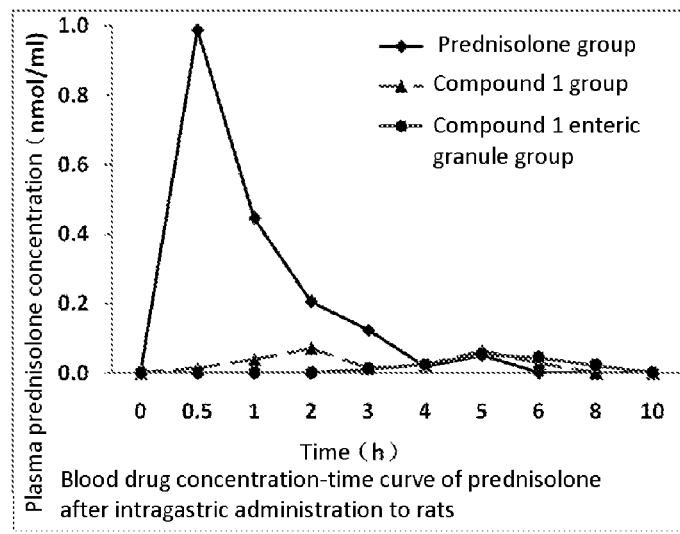
FIG. 3 shows the blood drug concentration-time curves of prednisolone for different groups of rats after intragastric administration.

For the prednisolone group, Compound 1 group, and Compound 1 enteric granule group, the plasma prednisolone concentration variation curves after the intragastric administration to rats are as shown in FIG. 3. As seen from the drug-time curves, as compared to free prednisolone group, the $C_{max}$ values were very low and the times to peak were significantly delayed for the Compound 1 group and Compound 1 enteric granule group.

For the Compound 1 group, a very low concentration of Compound 1 (10.4 ng/ml) could be detected in the rat plasma only at one time point of 0.5 h. After the administration of Compound 1 enteric granules, Compound 1 could not be detected at all time points. The research indicates that Compound 1 is only absorbed in trace amount at the stomach or the upper segment of small intestine in rat body, and the absorption of Compound 1 can be effectively prevented by using the enteric formulation technology to prevent the release at the stomach.

The Pharmacodynamic Effect of Intragastric Administration of Compound 1 to Ulcerative Colitis Models of Wistar Rat Induced by Enema with Trinitrobenzenesulfonic Acid (TNBS)

Comparison research among therapeutic effects of Compound 1 and a commercial formulation of prednisolone (prednisolone tablet, produced by Wuhan Yuancheng Co-Creation Technology Co., Ltd.) on ulcerative colitis models of Wistar rats after intragastric administration was carried out to further evaluate the improvement in main therapeutic effect indexes of the intragastric perfusion therapy of Compound 1 and compare it with that of treatment group with equivalent moles of a commercial formulation of prednisolone, thereby providing pharmacodynamic support for further development of Compound 1.

According to the experiment, 40 male Wistar rats (180-220 grams) were purchased, and randomly divided into four groups (i.e., physiological saline control group, model control group, prednisolone group and Compound 1 group), and there were 10 animals in each group. Except the physiological saline control group, ulcerative colitis animal models were produced by once enema administration of a mixed solution of 2.5% TNBS-50% ethanol (containing 80 mg/kg TNBS) to experiment animals in other three groups in an amount of 3.2 ml/kg. For the physiological control group, physiological saline was once administered by enema in an amount of 3.2 ml/kg. At 24 h after the modeling administration, the corresponding solvent control or therapeutic drugs were administered by enema depending on animal groups (qd×7d (one dose per day, for 7 days)), and detailed grouping and administration information is as shown in Table 14 below.

TABLE 14

Administration grouping and administration information of pharmacodynamic research on ulcerative colitis models of Wistar rat

| Group | Sample | Method and frequency of administration | Dosage (mg/kg) | Concentration (mg/mL) | Dose volume (mL/kg) | Animal number |
|---|---|---|---|---|---|---|
| Negative control group | Solvent | Intragastric perfusion (qd × 7) | — | — | 5 | 10 |
| Model control group | Solvent | Intragastric perfusion (qd × 7) | — | — | 5 | 10 |
| Prednisolone group | Prednisolone | Intragastric perfusion (qd × 7) | 1 | 0.2 | 5 | 10 |
| Compound 1 | Compound 1 | Intragastric perfusion (qd × 7) | 1.91 | 0.382 | 5 | 10 |

During the investigation, the main indexes to be observed include: death of animals, clinical observation, body weight, colon coefficient, histopathological examination of animals, and so on. For each experiment group, on Day 8 after modeling, animals were sacrificed. Colon tissues were collected to calculate the colon coefficient (colon coefficient=colon weight (g)/animal body weight (g) * 100%). Then histopathological examination and scoring were performed (histopathological scoring standard was shown in Table 15 below).

TABLE 15

Histopathological scoring standard for colon

| Evaluation index | Score | Characteristic observed with optical microscope |
|---|---|---|
| Inflammation degree | 0 | None |
| | 1 | Mild |
| | 2 | Moderate |
| | 3 | Severe |
| Inflammation area | 0 | None |
| | 1 | Mucosa layer |
| | 2 | Mucosa layer and submucosa layer |
| | 3 | Transmural property |
| Injury degree of intestinal crypt | 0 | None |
| | 1 | ⅓ of the base portion was injured |
| | 2 | ⅔ of the base portion was injured |
| | 3 | The crypt disappeared and the epidermis was complete |
| | 4 | The crypt disappeared and the epidermis was shed |

During the investigation, one animal was dead on Day 6 after modeling only in the model control group, and no abnormal death of animals was found in other groups.

The clinical symptoms of modeling animals were mainly: orange/yellow liquid at crissum, blood around nasal cavity, blood at canthus, arching back and piloerection, loose stool, lassitude, reduced activity, slow action, yellow/orange loose stool, brown loose stool, bloody loose stool, no stool, and so on.

Figure 4:
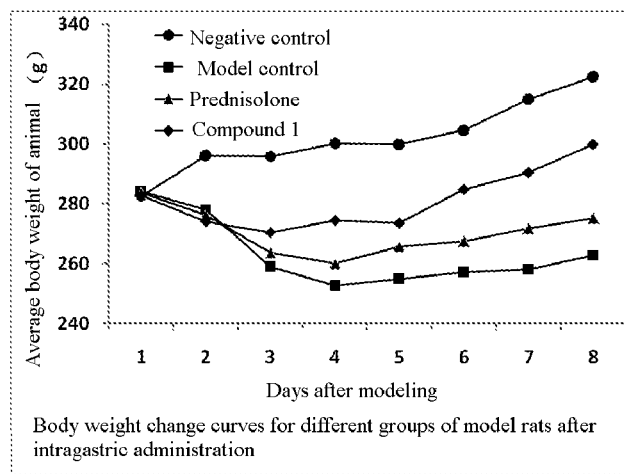
FIG. 4 shows the body weight change curves for different groups of model rats after intragastric administration.
Figure 5:
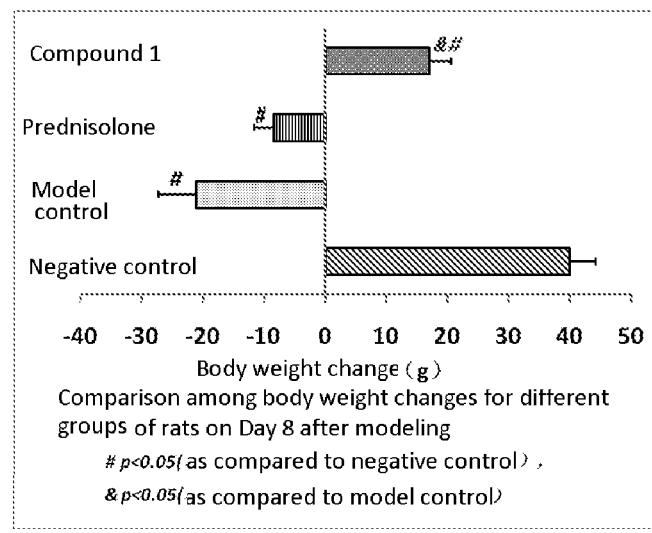
FIG. 5 shows a comparison among the body weight changes for different groups of rats on Day 8 after modeling.

As shown in FIG. 4, during the entire test, the body weights of animals in the control group kept on increasing; in contrast, the average body weights of animals in the model control group, prednisolone group and Compound 1 group all appeared to decrease significantly in the first 3 days after modeling, and the body weight began to rise on Day 4 after modeling for the Compound 1 group and on Day 5 after modeling for the other two groups. Here, the rising rate of the body weight for the Compound 1 group was higher than those for the other two groups. One-factor analysis of variance was further used to statistically compare body weight changes for different experimental groups on Day 8 after modeling (body weight change=body weight on Day 8 (g)–body weight on Day 1 (g)) (see FIG. 5, where * represents p<0.05 as compared to the negative control group, and # represents p<0.05 as compared to the model control group). The result shows that the increase amounts of animal body weight for three TNBS modeling groups were all significantly less than that for the physiological saline modeling negative control group; as compared to the model group, the body weight increases for the prednisolone group and Compound 1 group were both higher than that for the model group, but only the difference between the Compound 1 group and the model group was statistically significant. This result suggests that the therapeutic effect of Compound 1 on the ulcerative colitis rat model induced by TNBS enema is better than that of original form drug of prednisolone when used in the same moles.

Figure 6:
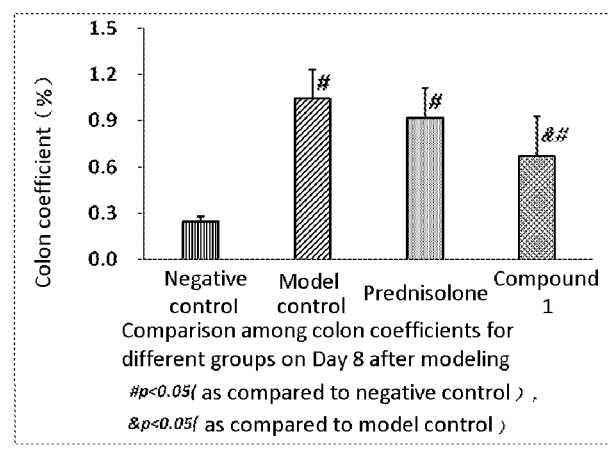
FIG. 6 shows a comparison among the colon coefficients for different groups of rats on Day 8 after modeling.

The index of colon coefficient was obtained on Day 8 after modeling after dissecting the animals. One-factor analysis of variance was used to compare the colon coefficients of animals in various experimental groups. The result is substantially in consistent with the analysis result of body weight change (see FIG. 6, where * represents p<0.05 as compared to the negative control group, and # represents p<0.05 as compared to the model control group). As compared to the negative control group, the colon coefficient of each model group was significantly increased (p<0.05). The increase amount for the model control group was the highest, the increase amount for the prednisolone group was less, and the increase amount for the Compound 1 group was the least. By further comparing the prednisolone group and compound 1 group with the model control group, the colon coefficient for the compound 1 group was significantly lower than that for the model control group (p<0.05), while the difference between the prednisolone group and the model control group was not statistically significant.

On Day 8 after TNBS modeling, the histopathological change of colon mainly appeared to be changes such as focal mucosa necrosis at descending colon site, neutrophil infiltration at mucosa layer and submucosa layer, edema, angiectasis, hyperemia, and so on.

Figure 7:
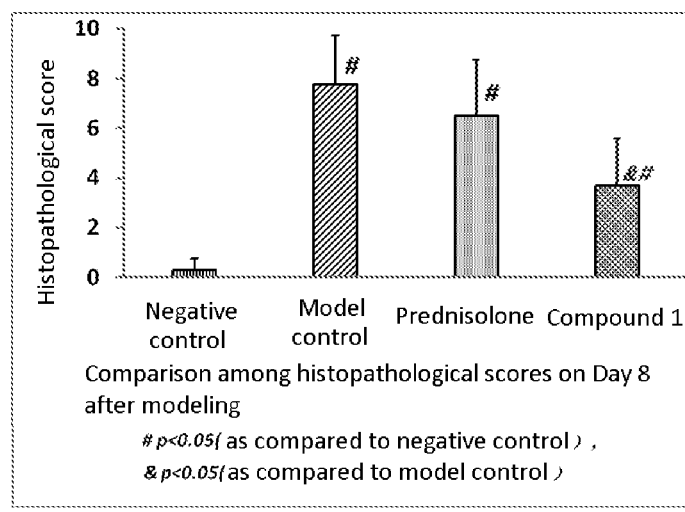
FIG. 7 shows a comparison among the histopathological scores for different groups of rats on Day 8 after modeling.

The one-factor analysis of variance result on histopathological scores of colons for various experimental animal groups was as shown in FIG. 7 (where * represents p<0.05 as compared to the negative control group, and # represents p<0.05 as compared to the model control group). As compared to the negative control group, the histopathological score of each model group was significantly increased (p<0.05). The increase amount for the model control group was the highest, the increase amount for the prednisolone group was less, and the increase amount for the Compound 1 group was the least. By further comparing the prednisolone group and compound 1 group with the model control group, the histopathological score for the Compound 1 group was significantly lower than that for the model control group (p<0.05), while the difference between the prednisolone group and the model control group was not statistically significant. This result is in consistent with the aforementioned body weight and colon coefficient analysis results, further suggesting that the therapeutic effect of intragastric administration of Compound 1 on ulcerative colitis rat model is better than that of prednisolone when used in an amount of equal moles.

Compound 1 was investigated above for systemic pharmacokinetics in animal body, localized pharmacokinetics in gastrointestinal tract, pharmacodynamic effect and the like. The results demonstrate that the lactuloside compound 1 according to the present disclosure can pass through the gastrointestinal tract of a mammal without being absorbed significantly by the gastrointestinal tract and hydrolyzed significantly by endogenous enzymes of a mammal host. Therefore, the lactuloside compound 1 can arrive at the colon site of the mammal, and release an active drug at the colon under the action of colon flora. The lactuloside compound 1 has a function of colon-localized drug release, and can be used for preventing or treating an intestinal disease.

It should be noted that other compounds (i.e., Compounds 2-17 listed in Table 1) were also experimentally investigated for systemic pharmacokinetics in animal body, localized pharmacokinetics in gastrointestinal tract, pharmacodynamic effect and the like in the present application. The results demonstrate that the lactuloside compounds 2-17 according to the present disclosure can also pass through the gastrointestinal tract of a mammal without being absorbed significantly by the gastrointestinal tract and hydrolyzed significantly by endogenous enzymes of a mammal host. Therefore, the lactuloside compounds 2-17 can also arrive at the colon site of the mammal, and release an active drug at the colon under the action of colon flora. The lactuloside compounds 2-17 have a function of colon-localized drug release, and can be used for preventing or treating an intestinal disease.

Although the present disclosure has been described in detail above with reference to the examples and comparative examples, it should be noted that the present disclosure is not limited to the examples and comparative examples. Variations or modifications on the present disclosure can be made without departing from the spirit and scope of the present disclosure.

What is claimed is:

1. A compound represented by Formula (I),

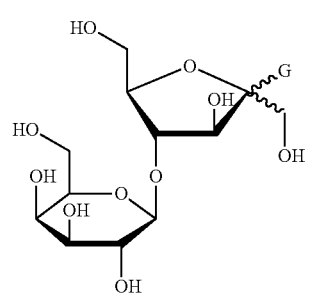

Formula (I)

wherein the lactulosyl group is connected to a heteroatom of genin (G) via a glycosidic bond, the genin (G) is a group formed by removing one hydrogen atom from a heteroatom of an active pharmaceutical molecule, and "⁓" indicates that the lactulosyl group is connected to the heteroatom of the genin (G) via an α-glycosidic bond or a β-glycosidic bond, wherein the genin (G) is selected from the group consisting of:

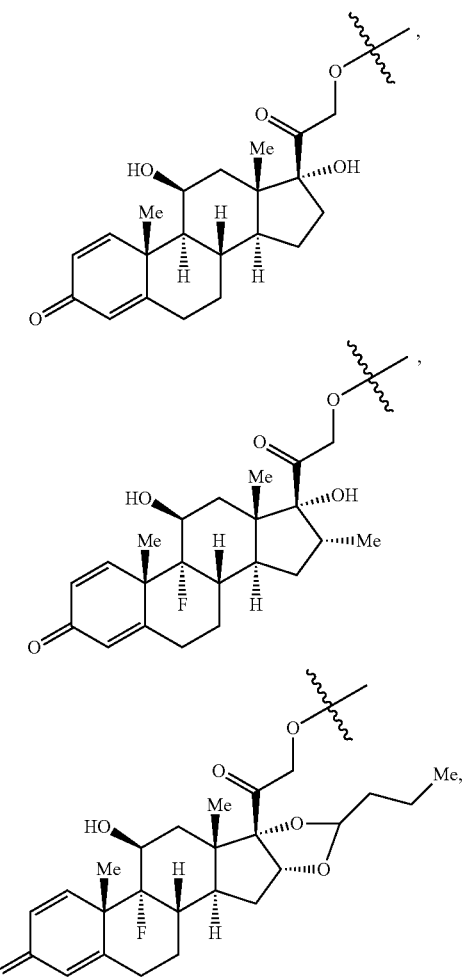

-continued

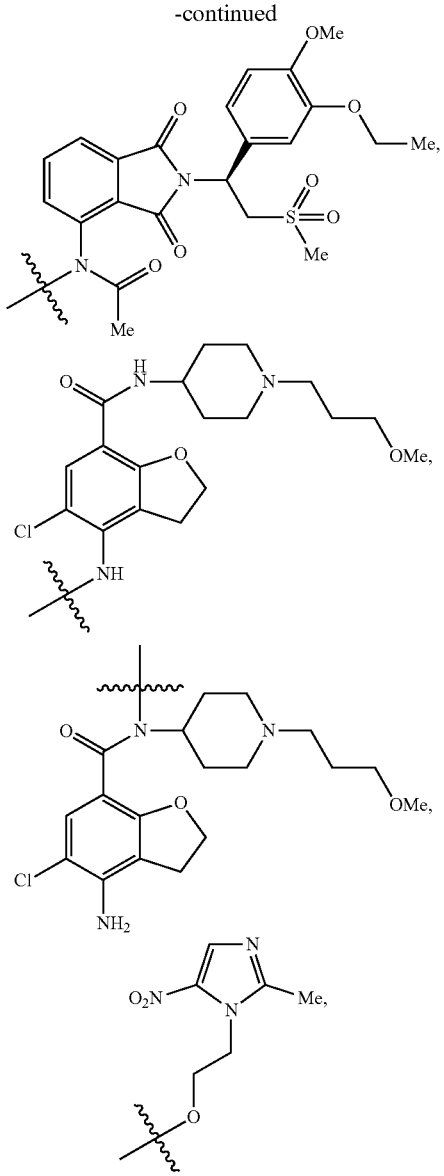

-continued

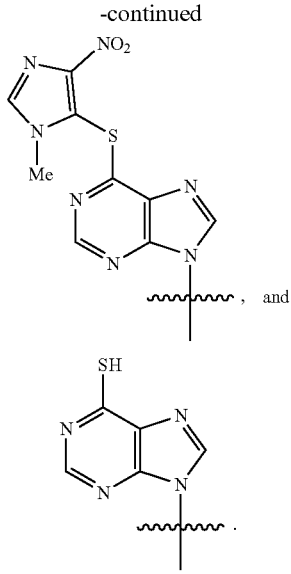

2. A pharmaceutical composition comprising a therapeutically effective amount of the compound according to claim 1, and at least one pharmaceutically acceptable carrier.

3. A method of treating an intestinal disease in a human, comprising administering to the human in need thereof the pharmaceutical composition according to claim 2, wherein the intestinal disease is selected from the group consisting of ulcerative colitis, Crohn's disease, infectious colitis, irritable bowel syndrome, chronic constipation, intestinal amebiasis, colon cancer, and rectal cancer.

4. The method according to claim 3, wherein the intestinal disease is selected from the group consisting of ulcerative colitis, Crohn's disease, and chronic constipation.

5. The pharmaceutical composition according to claim 2, wherein the pharmaceutical composition is an oral dosage form selected from the group consisting of a tablet, a pill, a capsule and syrup.

\* \* \* \* \*

UNITED STATES PATENT AND TRADEMARK OFFICE
CERTIFICATE OF CORRECTION

PATENT NO. : 11,491,232 B2  
APPLICATION NO. : 16/489238  
DATED : November 8, 2022  
INVENTOR(S) : Zhang et al.

Page 1 of 1

It is certified that error appears in the above-identified patent and that said Letters Patent is hereby corrected as shown below:

In the Claims

In Column 62, Claim 1, Lines 55-66, delete " 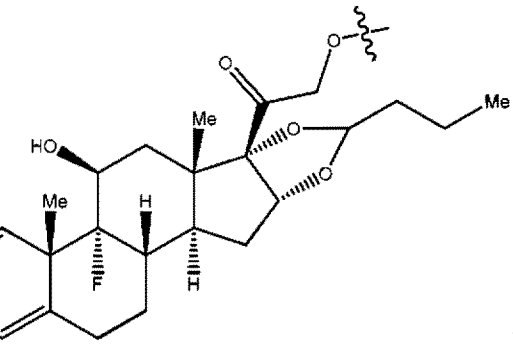 "

and insert -- 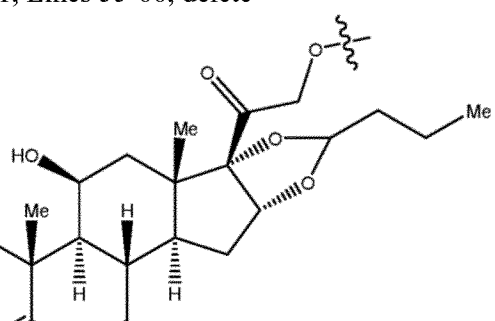 --, therefor.

Signed and Sealed this  
Seventh Day of February, 2023

Katherine Kelly Vidal  
*Director of the United States Patent and Trademark Office*